US006573362B1

(12) United States Patent
Kolanus et al.

(10) Patent No.: US 6,573,362 B1
(45) Date of Patent: *Jun. 3, 2003

(54) CYTHOHESIN-PH PEPTIDES THAT AFFECT THE ABILITY OF INTEGRINS TO ADHERE

(75) Inventors: Waldemar Kolanus, München (DE); Britta Ostner, München (DE)

(73) Assignee: Hoechst Aktiengesellschaft, Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 52 days.

(21) Appl. No.: 08/708,573

(22) Filed: Sep. 5, 1996

(30) Foreign Application Priority Data

Sep. 14, 1995 (DE) .......................................... 195 34 120

(51) Int. Cl.[7] ............................................. C07K 14/705
(52) U.S. Cl. ........................ 530/350; 530/395; 435/810
(58) Field of Search ........................ 424/278.1; 514/12; 530/350, 395; 435/810

(56) References Cited

U.S. PATENT DOCUMENTS 4,661,454 A 4/1987 Botstein et al. ............. 435/256
5,958,705 A * 9/1999 Staunton et al.

OTHER PUBLICATIONS

Kolanus et al Cell 86:233, Jul. 26, 1996.*
Ward et al. Therapeytic Immunology 1:165:1994.*
Albelda et al. FASEB J. 8:504.1994.*
Vgn de Langerlit Clinical Immunology J Immuno Patholoy, 73:123, 1994.*
Voet et al. *Biochemistry* Wiley & Sons, 1990 p. 126–127.*
Mikagama et al PNAS 90:10056, 1993.*
Lin Liu et al., "Cloning and sequencing of a human cDNA from cytolytic NK/T cells with homology to yeast SEC7", Biochemica et Biophysica Acta, 1992, pp. 775–778, vol. 1132, Elsevier Science Publishers B.V.
Auffray C. et al., "The Genexpress cDNA Program", Database EBI Online!, AC F00710, Apr. 7, 1995 XP002196101.
Waldemar Kolanus et al., "αLβ2 Integrin/LFA–1 Binding to ICAM–1 Induced by Cytohesin–1, a Cytoplasmic Regulatory Molecule", Cell, Jul. 26, 1996, pp. 233–242, vol. 86, Cell Press.
G. Walz et al., "Recognition by ElAM–1 of the Sialyl–Le$^x$ Determinant on Myeloid and Tumor Cells", Science, vol. 250., pp. 1132–1135., 1990.
M. S. Diamond et al., "The Dynamic Regulation of Integrin Adhesiveness", Current Biology, vol. 4, No. 6, 1994, pp. 506–517.
T. L. Collins et al., "Adhesion Receptors in Lymphocyte Activation", Current Opinion in Immunology, vol. 6, 1994, pp. 385–393.

Anon., "PH Domain: The First Anniversary", Elsevier Science Ltd, Sep. 1994, pp. 349–353.
T. A. Springer, "Traffic Signals for Lymphocyte Recirculation and Leukocyte Emigration: The Multistep Paradigm", Cell, vol. 76, Jan. 1994, pp. 304–314.
D. E. Shevell et al., "EMB30 is Essential for Normal Cell Division, Cell Expansion, and Cell Adhesion in Arabidopsis and Encodes a Protein that has Similarity to Sec7", Cell, vol. 77, Jul. 1994, pp. 1051–1062.
J. Gyuris et al., "Cdi1, a Human G1 and S Phase Protein Phosphatase that Associates with Cdk2", Cell, vol. 75, Nov. 1993, pp. 791–803.
S. Fields et al., "The Two–Hybrid System: An Assay for Protein–Protein Interactions", TIG, vol. 10, No. 8, Aug. 1994, pp. 286–292.
T. K. Kishimoto et al., "Cloning of the β Subunit of the Leukocyte Adhesion Proteins: Homology to an Extracellular Matrix Receptor Defines a Novel Supergene Family", Cell, vol. 48, 1987, pp. 681–690.
G. E. Moore et al., "Culture of Normal Human Leukocytes", The Journal of the American Medical Association, vol. 199, No. 8, Feb. 1967, pp. 87–92.
D. J. Rawlings et al., "Mutation of Unique Region of Bruton's Tyrosine Kinase in Immunodeficient XID Mice", Science, vol. 261, Jul. 1993, pp. 358–361.
J. L. Benovic et al., "cDNA Cloning and Chromosomal Localization of the Human β–Adrenergic Receptor Kinase" FEBS, vol. 283, No. 1, pp. 122–126.
S. Katzav et al., "vav, A Novel Human Oncogene Derived from a Locus Ubiquitously Expressed in Hematopoietic Cells", The EMBO Journal, vol. 8, No. 8, 1989, pp. 2283–2290.
W. Kolanus et al., "T Cell Activation by Clustered Tyrosine Kinases", Cell, vol. 74, Jul. 1993, pp. 174–183.
W. Tadmori et al., "Down Regulation of IL 2 mRNA by Antibody to the 50–kd Protein Associated with E Receptors on Human T Lymphocyte", The Journal of Immunology, vol. 36, No. 4, Feb. 1986, pp. 1155–1159.
L. Osborn et al., "Direct Expression Cloning of Vascular Cell Adhesion Molecule 1, a Cytokine–Induced Endothelial Protein that Binds to Lymphocytes", Cell, vol. 59, Dec. 1989, pp. 1203–1211.
S. Tsukada et al., "Binding of βγ Subunits of Heterotrimeri G Proteins to the PH Domain of Bruton Tyrosine Kinase", Proc. Natl. Acad. Sci. USA, vol. 91, Nov. 1994, pp. 11256–11260.

* cited by examiner

*Primary Examiner*—Phillip Gambel
*Assistant Examiner*—Jessica H. Roark
(74) *Attorney, Agent, or Firm*—Heller Ehrman White & McAuliffe, LLP

(57) ABSTRACT

Isolated cytohesin-PH peptides that can inhibit the beta-2 integrins from adhering, wherein the cytohesin-PH peptide has an amino acid sequence that comprises about a 140 amino acid domain from cytohesin-2. Assay kits comprising the peptides also are provided.

2 Claims, 42 Drawing Sheets

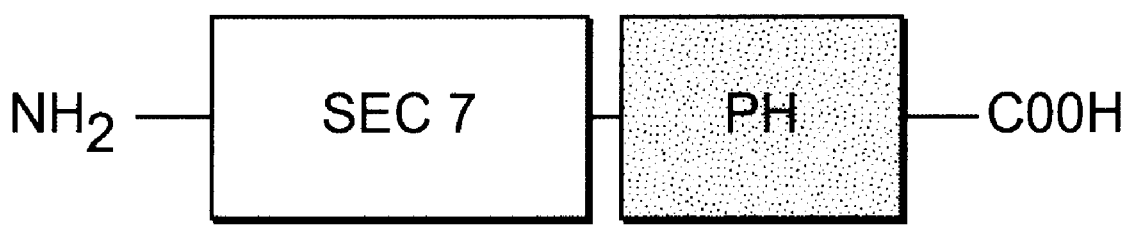
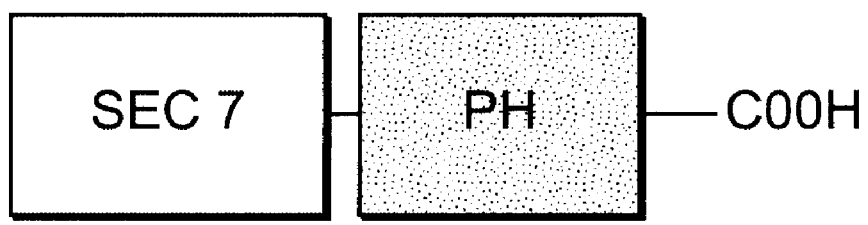
*FIG. 1A*

```
136  FTDLNLVQALRQFLWSFRLPGEAQKIDRMMEAFAQRYCQCNNGVFQSTDT  185
     |||||||||||||||||||||||||||||||||||||||||||||||||
  1  FTDLNLVQALRQFLWSFRLPGEAQKIDRMMEAFAQRYCLCNPGVFQSTDT   50

186  CYVLSFAIIMLNTSLHNPNVKDKPTVERFIAMNRGINDGGDLPEELLRNL  235
     ||||||||:|||||||||||:||||||:|||||||:|||||||||||||
 51  CYVLSFAVIMLNTSLHNPNVRDKPGLERFVAMNRGINEGGDLPEELLRNL  100

236  YESIKNEPFKIPEDDGNDLTHTFFNPDREGWLLKLGGGRVKTWKRRWFIL  285
     |:||:||||||||||||||||||||||||||||||||||||||||||||
101  YDSIRNEPFKIPEDDGNDLTHTFFNPDREGWLLKLGGGRVKTWKRRWFIL  150

286  TDNCLYYFEYTTDKEPRGIIPLENLSIREVEDSKKPNCFELYIPDNKDQV  335
     |||||||||||||||||||||||||||||:||.::|||||||||:|:.:
151  TDNCLYYFEYTTDKEPRGIIPLENLSIREVDDPRKPNCFELYIPNNKGQL  200

336  IKACKTEADGRVVEGNHTVYRISAPTPEEKEEWIKCIKAAISRDPFYEML  385
     |||||||||||||||||:|||||||||:||:|||||:|::|||||||||
201  IKACKTEADGRVVEGNHMVYRISAPTQEEKDEWIKSIQAAVSVDPFYEML  250

386  AARKKKVSSTKRH  398
     ||||:|:::.|:
251  AARKKRISVKKKQ  263
```

*FIG. 1B*

Cytohesin-1

```
       B   B B        B F         B F        B F     B        B   BB
       SA  SASH       SANHA       SANH       SANH    SH       ABSS
       RC  TCMH       TCUHC       RCUG       TH      CAPR
       BI  UIFA       UI4AI       BI4A       UA      IN1B
       11  1111       11H11       11H1       11      1221
        /   //         //          //         /       //
  1  GCGAGCGGGGCGCGGGGTGGCGCGGGAGCGCGGGACGCGGAGCGCGGAGCCGGAGCGCGGAGCCCGC    60
     ---+---------+---------+---------+---------+---------+---------+
     CGCTCGCCCCGCGCCCCACCGCGCCCTCGCGCCTCGCGCCTCGCGCCTCGGCCTCGGGCG

B   B  B     B   B       M    M    M    H
         SA  S  T     A   MB      A    N    G    
         RC  T  U     L   AS      E    L    A
         BI  C  H     U   ER           1
              M  C    1   21       3   1
                              //
                     A        MB
                     L        AS
                     U        ER
                     1        21
                      /        /

61  TCCCGCACCATGGAGGAGGACGACAGCTACGTTCCCAGTGACCTGACAGCAGAGGAGCGT       120
     ---+---------+---------+---------+---------+---------+---------+
     AGGGCGTGGTACCTCCTCCTGCTGTCGATGCAAGGGTCACTGGACTGTCGTCCTCCTCGCA a.a.  M   E   E   D   D   S   Y   V   P   S   D   L   T   A   E   E   R   -
```

```
                                  N    LP          CET L  S       PS  S      VUL
                                  L    AH          OCY A  L       OP  E      A9A
                                  1    31          111 3  1       15  1      264
                                   \    \           \   \  \       \   \      \
      AAAAACATGCAGAGGAACAAACAGGTAGCCATGGGCAGGAAAAATTTAATATGGACCCT
241   ------+---------+---------+---------+---------+---------+ 300
      TTTTTGTACGTCTCCTTGTTTGTCCATCGGTACCCGTCCTTTTTTAAATTATACCTGGGA a.a.    K  N  M  Q  R  N  K  Q  V  A  M  G  R  K  K  F  N  M  D  P  -

BB  S                                               B        E
           ABB BASNA     A  M                              M   SM     BBC
           LSS SMTLU     L  S                              N   RB     SBO
           WLL RHYA3     W  E                              L   DO     RS5
           111 1114A     1  1                              1   12     117
            \\   \\      \  \                              \    \      \
      AAAAAGGGGATCCAGTTCTTAATAGAGAACGACCTCCTGAAGAACACTTGTGAAGACATT
301   ------+---------+---------+---------+---------+---------+ 360
      TTTTTCCCCTAGGTCAAGAATTATCTCTTGCTGGAGGACTTCTTGTGAACACTTCTGTAA a.a.    K  K  G  I  Q  F  L  I  E  N  D  L  L  K  N  T  C  E  D  I  -

B                                                        AMSS
           BS
          FIG. 2C

M
```

```
                                                       BO2                                                    AP                                          VAET
                                                                                                              N1                                          RECY
                                                                                                              22                                          2111
                                                                                                              /                                           //
      361 GCCCAGTTCTTATATAAAGGCGAAGGGCTCAACAAGACAGCCATCGGGGACTACCTAGGG 420
          ----+----+----+----+----+----+----+----+----+----+----+----+
          CGGGTCAAGAATATATTTCCGCTTCCCGAGTTGTTGTCTGTCGGTAGCCCTGATGGATCCC a.a.  A  Q  F  L  Y  K  G  E  G  L  N  K  T  A  I  G  D  Y  L  G  -

BS                  BN N            F         SAU3A
                                SC                  BL S           AN         NLA3
                                TR        MM        VA I           LU         1H
                                NF        SB        13 1           U4
                                11        EO                       1H
                                          12                       1
                                /                   /              /
      421 GAGAGAGATGAGTTAATATCCAGGTTCTTCATGCATTTGTGGAGCTGCATGAGTTCACT 480
          ----+----+----+----+----+----+----+----+----+----+----+----+
          CTCTCTCTACTCAAATTATAGGTCCAAGAAGTACGTAAACACCTCGACGTACTCAAGTGA a.a.  E  R  D  E  F  N  I  Q  V  L  H  A  F  V  E  L  H  E  F  T  -

```
                                                                    A  HNC  A
                                              L     A  H  M         L  PCR  U
              SM           SC                 W     L  P  N         U  AIF  9
              AS           TR                 N     U  A  L         1  211  6
              BE           NF                 1     1  2  1         /        /
              11           11                 /     /  /  /
     GATCTTAATCTCGTCCAGGCACTACGGCAGTTCCTGTGGAGCTTCCGGCTACCCGGAGAG
481  ---------+---------+---------+---------+---------+---------+ 540
     CTAGAATTAGAGCAGGTCCGTGATGCCGTCAAGGACACCTCGAAGGCCGATGGGCCTCTC a.a.  D  L  N  L  V  Q  A  L  R  Q  F  L  W  S  F  R  L  P  G  E   -

S    BB                         F
              A    SSHMM  B                   O
              U  T AIPNB  S                   K
              3  A WEALO  L                   1
              A  Q 11212  1                   /
              /  /  /     /
     GCCCAGAAGATCGACCGGATGATGGAGGCCGTTTGCCCAGCGATATTGTCAGTGCAATAAT
541  ---------+---------+---------+---------+---------+---------+ 600
     CGGGTCTTCTAGCTGGCCTACTACCTCCGCAAACGGGTCGCTATAACAGTCACGTTATTA a.a.  A  Q  K  I  D  R  M  M  E  A  F  A  Q  R  Y  C  Q  C  N  N   -

```
            S          ES                  A  A           N  S S   L  S
            R          CL                  E  E           L  G L   A  R
            1          11                  3  2           1  1 1   3  1
      GGCGTGTTCCAGTCCACGGATACTTGTTACGTCCTCCTTTGCCATCATCATGTTGAAC
 601  ---------+---------+---------+---------+---------+---------+  660
      CCGCACAAGGTCAGGTGCCTATGAACAATGCAGGAGGAAACGGTAGTAGTACAACTTG a.a.   G  V  F  Q  S  T  D  T  C  Y  V  L  S  F  A  I  I  M  L  N   -

B     M M   N
                                                      S     M M   L
                                            M         R     N S   L  A
                                            N         D     L L   1  3
                                            L         1     1 1   /
      ACCAGTCTGCACAACCCCAATGTCAAAGATAAGCCCCACTGTGGAGAGGTTCATTGCCATG
 661  ---------+---------+---------+---------+---------+---------+  720
      TGGTCAGACGTGTTGGGGTTACAGTTTCTATTCGGGGTGACACCTCTCCAAGTAACGGTAC a.a.   T  S  L  H  N  P  N  V  K  D  K  P  T  V  E  R  F  I  A  M   -

E   B        B H B B     H
         S    B                      C H B        A B S G S S H S I T    M
         F   B S  M                                              FIG. 2F
      S
```

```
                    A    SM   N            OPS  P    L  APIAPPANF    N
              E     N    AA   L            NAL  M    U  N1AWEACFI    L
              C     1    11   1            121  1    1  221112111    1
      AACCGAGGCATCAATGATGGGGAGACCTGCCGGAGAGCTCCTCCGAATCTCTATGAG
721   ----+----+----+----+----+----+----+----+----+----+----+----+   780
      TTGGCTCCGTAGTTACTACCCCTCTGGACGGCCTCTCGAGGAGGCCTTAGAGATACTC a.a.   N  R  G  I  N  D  G  G  D  L  P  E  E  L  L  R  N  L  Y  E  -

MD                                    M    M
                          SR                    B    M    B     B    N
                          EA                    B    B    S     O    L
                          11                    1    2    1     2    1
      AGCATAAAAAATGAACCCTTTAAAAATCCCAGAAGACGGGAATGACCTCACTCACACT
781   ----+----+----+----+----+----+----+----+----+----+----+----+   840
      TCGTATTTTTTACTTGGGAAATTTTAGGGTCTTCTGCCCTTACTGGAGTGAGTGTGA a.a.   S  I  K  N  E  P  F  K  I  P  E  D  D  G  N  D  L  T  H  T  -

```
841 TTCTTCAATCCAGACCGAGAAGGCTGGCTATTGAAACTCGGAGGTGGCAGGGTAAAGACT 900
    ----------+---------+---------+---------+---------+---------+
    AAGAAGTTAGGTCTGGCTCTTCCGACCGATAACTTTGAGCCTCCACCGTCCCATTTCTGA a.a. F F N P D R E G W L L K L G G G R V K T -
                B          M H                    AX    S
                SE         B G                    CC    E
                MS         O A                    CA    C
                AP         2 1                    11    1
                13         /                      //

901 TGGAAGAGACGCTGGTTCATTCTGACTGACAACTGCCTTTACTACTTTGAGTATACCACG 960
    ----------+---------+---------+---------+---------+---------+
    ACCTTCTCTGCGACCAAGTAAGACTGACTGTTGACGGAAATGATGAAACTCATATGGTGC a.a. W K R R W F I L T D N C L Y F E Y T T
      B        H       H   D       S     H    H
      N FBSS   IT      IT  D       HMNC  BP   I
      L OAPE   NF      NF  E       PNCR  SL   N
      A KN1C   FI      FI  1       ALIF  LE   F
      4 1221   11      11  /       2111  11   1
        //     /       /           ///
```

FIG. 2H

```
    961 GATAAGGAGCCCCGTGGAATCATCCCTTTAGAGAATCTGAGTATCCGGGAAGTGGAGGAC      1020
        ----------+---------+---------+---------+---------+---------+
        CTATTCCTCGGGGCACCTTAGTAGGGAAATCTCTTAGACTCATAGGCCCTTCACCTCCATG a.a.     D  K  E  P  R  G  I  I  P  L  E  N  L  S  I  R  E  V  E  D  -

A
                                              L
                                              U
                                              1
   1021 TCCAAAAAACCAAAACTGCTTTGAGCTTTATATCCCCGACAATAAAGACCAAGTTATCAAG      1080
        ----------+---------+---------+---------+---------+---------+
        AGGTTTTTTGGTTTTGACGAAACTCGAAATATAGGGGCTGTTATTTCTGGTTCAATAGTTC a.a.     S  K  K  P  N  C  F  E  L  Y  I  P  D  N  K  D  Q  V  I  K  -

HSM       S       MA       N        B   BS     D
        ATN       E       NC       L       SH   SA     D
        EUL       C       LI       A       AP   TU     E
        311       1       11       4       WA   Y3     1
                                            12  1A
                                               /
   1081 GCCTGCAAGACCGAGGCTGACGGGGTGGTGGAGGGAACCACACTGTTTACCGGATC           1140
        ----------+---------+---------+---------+---------+---------+
```

*FIG. 21*

```
                 CGGACGTTCTGGCTCCGACTGCCCGCCACCACCTCCCCTTGGTGTGACAAATGGCCTAG
a.a.              A  C  K  T  E  A  D  G  R  V  V  E  G  N  H  T  V  Y  R  I  -

A    ASM   H                  M              BF           B
                   AAM        A    VEN   G                  S              SN           S
                   LLN        H    ACL   A                  E              MU           L
                   UWL        A    111   1                  1              F4           1
                   111        2                                            1H
                   /                                                       /
      TCAGCTCCGACGCCCGAGGAGGAGTGGATTAAGTGCATTAAAGCAGCCATCAGC
1141  ------+---------+---------+---------+---------+---------+  1200
      AGTCGAGGCTGCGGGCTCCTCCTCACCTAATTCACGTAATTTCGTCGGTAGTCG a.a.   S  A  P  T  P  E  E  K  E  E  W  I  K  C  I  K  A  A  I  S  -

PS              F                        B              B
                   B   ADNNPA      N                        BS             M
                   B   VRLLUU      U                        SM             N
                   V   AAAAM9      4                        AA             L
                   1   224416      H                        11             1
                   /   ////                                 /
      AGGGACCCTTTCTACGAAATGCTCGCAGCACGGAAAAAGAAGGTCTCCTCCACGAAGCGA
1201  ------+---------+---------+---------+---------+---------+  1260

FIG. 2J
```

```
         TCCCTGGAAAGATGCTTTACGAGCCTGCCTTTTCTTCCAGAGGAGGTGCTTCGCT
a.a.     R  D  P  F  Y  E  M  L  A  A  R  K  K  K  V  S  S  T  K  R  -

1320
                      F                           S           BH          ESA
                      N  SS        B      B A    DNHASSM   A BSGS         AAC
                      U  ET        B      S C    RLAUETB   L APIA         RPI
                      4  CY        V      G I    AAE9CYO   U N1AC         111
              D       H  11        1      1 1    2436112   1 2211         111
              D                                     /         /            /
              E                                     /         /            /
              1                                     /         /            /
      CACTGAGCCGTGCAGCCAAGGCGGTTGGTCCTGCGGGGCCTTGGAGCTCCTGCTCTTCTCC
1261  ------+---------+---------+---------+---------+---------+---- 1320
      GTGACTCGGCACGTCGGTTCCCGCCAACCAGAGCGCCCCGGAACCTCGAGGACGAGAAGAGG
a.a.  H  *

E  BS       S     BESH
                  F  H                              C  BSCDHMNAA SBSCCIT
          F  M    N  O  G                           O  STRRANLCU ESTORNF
          N  U    U  4  K  A                        N  LNFAELAI9 CLN5FFI
      S   L  H    4  H  1  1                        1  111231416 1117111
      F M N B S S N                                      /  /   /  /  /
      A S C B E T L                                      /  /   /  /  /
      N L O V C Y A                                      /  /   /  /  /
      1 1 1 1 1 1 3
       / / / / / / /
      CGCACCTCCATGGATGCACTGCTGCCGAGCAGAGGCGTCCTCTGCCAGGCCCCGCCCCTGA
1321  ------+---------+---------+---------+---------+---------+---- 1380
```

*FIG. 2K*

```
                                                                         GCGTGGAGGTACCTAGCGTGACGACGGCTCGTCTCGCAGGAGACGGTCCGGGGCGGGGACCT

B               M  A       A
      SM              A  L       L
      MA              E  U       U
      AE              1  1       1
      1 1

1381  TTCCTAGAGACTAGCTTCAGCTTTTTGCTATTTTTTTAAGTGGGAGAAGGGTGGGCAGTT    1440
      ----+----|----+----|----+----|----+----|----+----|----+----
      AAGGATCTCTGATCGAAGTCGAAAACGATAAAAAAAATTCACCCTCTTCCCACCCGTCAA

M
                                                          S
                                                          E
                                                          1

SC
              AAFHEBHM                               B
      M E B   VURPAPAB                             N NBS
      N A S   A91AEMEO                             L LAP
      L R R   26021132                             A AN1
      1 1 1       /                                3 422
          /                                           /

1441  ATCACTGGGAAGAGAGAGGACCGGCCACCTGTCCAGCATGGGCTCCAGAGCCTTCCTCTCT    1500
      ----+----|----+----|----+----|----+----|----+----|----+----
      TAGTGACCCCTTCTCTCTCCTGGCCGGTGGACAGGTCGTACCCGAGGTCTCGGAAGGAGAGA
```

*FIG. 2L*

```
           BH                 F      B S
         A BSGS               N      BSECBBHM           D
         L APIA               U      STARABAN           D
         U N1AC               4      RNEFLVEL           E
       M 1 2211               H      11111131           1
       N                             
       L  /  /                /       /      /          /
       1
       CACAGGGGCAGAGCTCTTGTCGGCAGGGCAGCCTCCTGGCCAGTTTCTCTGCTCAGTGTTC
1501   ------+---------+---------+---------+---------+---------+  1560
       GTGTCCCCGTCTCGAGAACAGCCGTCCCGTCGGAGGACCGGTCAAAGAGACGAGTCACAAG

B     M
                                                            S     B
                                                            M     O
                                           M   B    S       F     2
                                           N   S    G       1
           BH                              L   L    1
         A DBSGS                           1
         L DAPIA                            /  /    /        /     /
         U EN1AC
       B 112211
       H  / / /

TGGTAGCAGAGCTCAGAGCCAACTGTTTACCTCTTGGTTGTCCCGTGAAGAAGCCTTCA
1561   ------+---------+---------+---------+---------+---------+  1620
       ACCATCGTCTCGAGTCTCGGTTGACAAATGGAGAACCAACAGGGCACTTCTTCGGAAGT

```
1621 AACCCTGCACCATAAATACATGTGTCCATATATTATTATATGTTAAGAGAAAAAGGTGGA 1680
     ---------+---------+---------+---------+---------+---------+
     TTGGGACGTGGTATTTATGTACACAGGTATATAATAATATACAATTCTCTTTTTCCACCT
              3    31                          1
                   /
          E        M            BS
          A        B            BSA            M    M
          R        O            GTU       M    S    A
          1        2            LY3       B    E    E
                                21A       O    1    2
                                //        2
1681 AAGGAAGAGAAGCCACATACTATAAAGATCTATTTTTTTTTAAGAGAGAACGTAGGG 1740
     ---------+---------+---------+---------+---------+---------+
     TTCCTTCTCTTCGGTGTATGATATTTCTAGATAAAAAAAAAAATTCTCTCTTGCATCCC
          B  B                BS  F   N   H   H   A
          S  B                SC  U   F   A   H   L   U
          M  V                ETR 4   C   1       1   1
          1  1                CNF                    
                              11

BHBS
                                      BS                SGSC
                                      SCES   B    B    PITR
                                      SETRAA B    V    1ANF
                                      CNFRP  1    1    2111
                                      11111            /
1741 CTGTTCAGGTGCATTCTGCCCTGGCTGCGCGTGGGAGCTTCCCTGGAGAAGAGCACCT 1800
     ---------+---------+---------+---------+---------+---------+
     GACAAGTCCACGTAAGACGGGACCGACGCGCACCCTCGAAGGGACCTCTTCTCGTGGA
```

```
                                                                                              1   1  1 63                              4      1                                                          11                    24316  11
                                                                                              1                                                                                                                                    //
1921                                                                                          CGCAGAGGGCAGAGGCCCAGTGGAGCCTCAGACGGCACAGTCAGAGTCGGGGGCCTGCCT           1980
                                                                                              ----+----+----+----+----+----+----+----+----+----+----+----+
                                                                                              GCGTCTCCCGGTCTCCGGGTCACCTCGGAGTCTGCCGTGTCAGTCTCAGCCCCCGGACGGA

SS                F  F        B  BH           S   B    N S            F    O
                                                                                                     EHHBNCCSS          N  N        B  BP           F ASSABFSSF             K
                                                                                                     AAPSCRREF          U  U        V  VA           A  CETCSOPAA
                                                                                                     EEALIFFCI          4  4        1  12           N  ICUIGKBCN
                                                                                                     132111111          H  H                        1  111111221            1
                                                                                                     /////                                            /////

1981                                                                                          GGCCGGGGTCGCAGTCGGCAGCAGCGTGCAGTCCGGCATCTCCCGCGATGCTTTCCAT           2040
                                                                                              ----+----+----+----+----+----+----+----+----+----+----+----+
                                                                                              CCGGCCCCAGCGTCAGCCGTCGTCGCACGTCAGGCCGTAGAGGGCGCCTACGAAAGGTA

B                   B   A        E        M H
                                                                                                   M A   MNABSS          S   L        BC       A G
                                                                                                   N C   NLVAPE          L   U        SO       E A
                                                                                                   L I   LAAN1C          1   1        R5       2 1
                                                                                                   1 1   141221                       17
                                                                                                           //                          /
```

*FIG. 2P*

```
         CCCAAGTGCCTGCGGAGCCCGAGGAGAGAGAGCTGACTGGACGCTTACGTTATTTTC
2041     ----+----+----+----+----+----+----+----+----+----+----+----+ 2100
         GGGTTCACGGACGCCTCGGGCTCCTCTCTCTCGACTGACCTGCGAATGCAATAAAAG

H   X    MD                                                A
              IMT C    SR                                                L
              NNF M    EA                                                U
              FLI 1    11                                                1
              111 /                                                      /
         CTCCTTCAGAATCCAAGTTCTGTTGGGCTTTAAAGTAGAAAGTCAGCATTTTCCTTGAG
2101     ----+----+----+----+----+----+----+----+----+----+----+----+ 2160
         GAGGAAGTCTTAGGTTCAAGACAACCCGAAATTTCATCTTTCAGTCGTAAAAGGAACTC

B        M              BB
                         S        N              NSSH
              M          M        L              LAPP
              N          F        1              AWEA
              L          1                       4112
              1                                   //
         CTAAATACCTAATAACCAAAAACTGTGAGGAAGGTTATCGGGACAGAGGTTCCGGATAACC
2161     ----+----+----+----+----+----+----+----+----+----+----+----+ 2220
         GATTTATGGATTATTGGTTTTGACACTCCTTCCAATAGCCCCTGTCTCCAAGGCCTATTGG
```

TGTTTCATTTTGGGTTTTCTTCCCTCTTCCCCAGACTCCAGTCCTCGTTCTAGAGGAAGGA
2221 ---+---------+---------+---------+---------+---------+---------+ 2280
        ACAAAGTAAAACCCAAAGAAGGAGAAGGGGTCTGAGGTCAGGAGCAAGATCTCCTTCCT

E    S                        A   A                           M
        C    A                        L   L                           N
        O    U                        U   U                           L
        5    3                        1   1                           1
        7    A

GTAGGACTTCCCCGATCCCCCGTAGCTTTCAGCTTTTTCTGCCTCAAAAACCAGCCCTAACTG
2281 ---+---------+---------+---------+---------+---------+---------+ 2340
        CATCCTGAAGGGGCTAGGGGCATCGAAACTCGAAGTCGAAAAAGACGGAGTTTTGGTCGGGATTGAC

```
                                                                        F       B
                                                                        N       SS
                                                                        A       ET
                                      H   D                    F   A    L       C N
                              B       I   D                    N   L    W     B B V 1 1
                      B       D P     N   F                    U   4    N     A C I 1 1
              F       B S     D L                              4   H    1     B V 1
              N       B M     E E                              H   1          1
              U       V F     1 1
              4       1 1
              H
      CTGCAGGGCGCTGTGTGAGCTGGCCCTGCCCCTCCTCATTACAGTATGAAGGGAGCCGTGA
2461  ---------+---------+---------+---------+---------+---------+ 2520
      GACGTCCGCGACACACTCGACCGGGACGGGGAGGAGTAATGTCATACTTCCCTGGCACT

CACGCAGCATTTCCTGCCGTTCTCTCAGGGACTCTCAGGCAGCTCCTGCCACTCCGCC
2521  ---------+---------+---------+---------+---------+---------+ 2580
              GTGCGTCGTAAAAGGACGGCAAGAGAGTCCCTGAGAGTCCCGTCGAGGACGGTGAGGCGG
      S S                                              B
      C A   H   B                   N   B S B          E S   A
      R U   A   S                   N S S S C S        A S   C
      F 9   E   R                   L P P T R P        E M   I
      1 6   3   1                   A H H N F M    E H P A   1
                                    3 1 1 1 1 1    A A 3 1
                                                   E E 1
                                                   1 3

AGGGCCAGCATGCCAGTCCAGGAGCAGGAGCAGGTGGCTGGCTGTCTTGCGCTCTCGCCCCCGC
2581  ---------+---------+---------+---------+---------+---------+ 2640
```

FIG. 2T

```
                   TCCCGGTCGTGTACGGTCAGGTCCGTCTCGTCCACCGACCGGACAGAGACCGGCAGAGCGGGGCG

F
                              PBS  ES BSS        M HNM        AS S  BMBBB
                         B    ADMNPSAACABSCCSSA  N HUN     F  VE P  SNBSB
                         S    VRNLUTUVOUSTRREEC  L A4L     B  AC M  LLVGV
                         L    AALAMN9AN9LNFFCCI  1 1H1        11 1  11111
                         1    22141162161111111  /  /            /  /

CCCTCCACAGGACCCTGGACCAGGGCGGTGCAGGGCGCAGCCCCGAGGAGGCAGGTGGAG                    2700
                    2641 ----+---------+---------+---------+---------+---------+
                         GGGAGGTGTCCTGGACCTGGTCCCGCCACGTCCCGCGTCGGGGCTCCTCCGTCCACCTC

S       FB                   S
                    F    A               H  A   HANS              S  E   NA        M
                    AN   C               G  U   ACUT              E  C   LL        N
                    LU   I               A  9   EI4U              C  1   AW        L
                    U4   1               1  6   31H1              1      41        1
                    1H   /                  /   //                       /         /

GAGCTGGCGGGTTTTCACAGGGCTGCGCAGGGCTCCCTCTGATCCTTTAGGGTTGGCG                    2760
                    2701 ---------+---------+---------+---------+---------+---------+
                         CTCGACGCCCAAAAGTGTCCCGACGCGTCCCGAGGAGACTAGGAAATCCCAACCGC

FIG. 2U
```

```
           S           MA         M         M S              H       E M
           F           NL         N         N N M            P       A A
           A           LU         L         L F              H       M E
           N           1 1        1         1 1              1       1 3
       AGCATCTCTGGAAATAGCTTTTGCAGAGAGTGGTGGAGGAATAGAGGGGGACAGTCTG
2761   -----+---------+---------+---------+---------+---------+  2820
       TCGTAGAGACCTTTATCGAAAACGTCTCCCACCACCTCCTTATCTCCCCCTGTCAGAC

BS      BC
                      AD         SAM     SC
           AM     M   LR         TUN     TR         B             B M
           CN     N   WA         Y3L     NF         S             P S
           IL     L   1 3        1A1     1 1        P             M L
           1 1    1   /          /                                1 1
       TCACCCTCCCTCCCCCGCCACTTTGTGTAGAGATCCTACCTGGAGGAATGGCTTTAGGCACTT
2821   -----+---------+---------+---------+---------+---------+  2880
       AGTGGAGGGAGGGGGCGGTGAAACACATCTCGGATGGACCTCCCTTACCGAAATCCGTGAA

S    BS
           M    A    MM    E            HANA  SCM
           N    L    AN    A            PVLU  TRB
```

FIG. 2V

```
                                              L         U           EL    R           HAA9  NFO
                                              1         1           31    1           1246  112
                                              /         /           //    /           ////  ///
       TTGTGCCAGAGCTTGTGAGGGTGACAGAAGAGGTCCAGGCTGGAAACCTGAACTTTCTG
2881   ------+---------+---------+---------+---------+---------+   2940
       AACACGGTCTCGAACACTCCCACTGTCTTCTCCCAGGTCCGACCTTTGGACTTGAAAGAC

S   BS       BMN                 S     B              S    C
            E   SCE      ANL                 E     S              A    FHH          N
            X   TRC      NLA                 C     L              U    RAP          L
            A   NFO      114                 1     1              9    1EA          A
            1   11K      /                   /     /              6    032          4
            /   ///                                                /    ///          /
       GGTGGGAGAACCAGGTGGTGCCTGCCGAGGTCTGCCGAGGTCTGTTTGGGCCGGTGCTGGAGCC
2941   ------+---------+---------+---------+---------+---------+   3000
       CCACCCTCTTGGTCCACCACGGACGGCTCCAGACCCGACACAAACCCGGCCACGACCTCGG

BS
         N   S                              BB B   SSSSSS                  MM  B N SSC
         A SPAHAHBNDHNABBSSBSHNAACCCCCSSSS                                 NA  A L ETR
         LPVUAVPPCRACPASPTSTALUURRREEMR                                    LE  N A CNF
         UBU9EAAMIAEIANL1NLNEA99FFFFCCAF                                   11  1 4 111
         122631211231112121113466111111111                                 //  / / ///
         /////////////////////////////////
```

FIG. 2W

```
3001  TGTCCAGCTGGCCCGGGCCCTGGCCTGGTTCTCAAGTGTGTTCCTAGACAGAGAGGCACCT  3060
      ------+---------+---------+---------+---------+---------+
      ACAGGTCGACCGGGCCCGGGACCGGACCAAGAGTTCACAAAGGATCTGTCTCTCCGTGGA

M
                                                              N
                                                              L
                                                              1

3061  GGGTCAGTATTAGTCTCTATTTATCAGAGGTGTAAATAATCTATGTATAGTTTTTCTCCTTT  3120
      ------+---------+---------+---------+---------+---------+
      CCCAGTCATAATCAGATATAAATAGTCTCCACATTTATTAGATACATATCAAAAAGAGGAAA

MD
                SR
                EA
                11

3121  TAGATTATTTTGTATTTGTTTAAAGAAGTTTTGTCAAAATACAAAAATATAAAGAAATG  3180
      ------+---------+---------+---------+---------+---------+
      ATCTAATAAAACATAAACAAATTTCTTCAAAACAGTTTTATGTTTTATATTCTTTAC
```

FIG. 2X

```
                      H                           M           T   T
                      I                           S           S   S
                      N                           E           P   P
                      C                           1           5   5
                      2
     ACTGAAAGTTGTTGACAGGGTTTTTAAGAAATAATTATTCTAATTGTTTTTGTTTGTTTG
3181 ----+----+----+----+----+----+----+----+----+----+----+----+ 3240
     TGACTTTCAACAACTGTCCCAAAAATTCTTTATTAATAAGATTAACAAAAACAAACAAAC

F
                           M    HHSS  S NP           B B
                           A    HAET  F US           B V
                           E    AECY  C 4T           V 1
                           1    1211  1 H1

TTTTTGCCTTGTAAACTAGCGCCAAGGAACTGCAGCAAATAAACTCCAACTCTGCCCAAG
3241 ----+----+----+----+----+----+----+----+----+----+----+----+ 3300
     AAAAACGGAACATTTGATCGCGGTTCCTTGACGTCGTTTATTTGAGGTTGAGACGGGTTC

CAAAAAAAAAA
3301 ----+----+- 3311
     GTTTTTTTTTT
```

FIG. 2Y

Cytohesin-2 (cts 18.1)

```
                                              B
                                              s
                                              u
                           B                  3        B
                           s                  6        s
                           s                  I        g
                           6                           I
                           I
   catgagttcaccgacctcaatctggtgcagtccctcaggcagtttctatggagctttcgc
19 -+---------+---------+---------+---------+---------+--------- 78
   GTACTcaagtggctggagtttagaccacgtcaggagtccgtcaaagatacctcgaaagcg
``` a.a.  H  E  F  T  D  N  L  V  Q  S  L  R  Q  F  L  W  S  F  R  -

```
           B                          HS
           s                          at
           a                          eu
           W                          II
           I                           /
   ctacccggagaggcccagaaaattgaccggatgatgatggaggccttcgcccagcgatactgc
79 -+---------+---------+---------+---------+---------+---------- 138
   gatgggcctctccgggtcttttaactggcctactactccggaagcgggtcgctatgacg
``` a.a.  L  P  G  E  A  Q  K  I  D  R  M  M  E  A  F  A  Q  R  Y  C  -

FIG. 3A

```
                                            A
                                            f  B
                                            l  sP
                                            I  am
                                            I  Al
                                            I  II
                                            /
        ctgtgcaacccctggggtttccagtccacagacacgtgctatgtgctgtcttcgccgtc
    139 -+---------+---------+---------+---------+---------+--------- 198
        gacacgttgggaccccaaaggtcaggtgtctgtgcacgatacacgacaggaagcgggcag a.a.     L  C  N  P  G  V  F  Q  S  T  D  T  C  Y  V  L  S  F  A  V  -

E
                                                                    c
                                        B                           o   H
                                        s                           4   a
                                        b                           7   e
                                        I                           I   I  I
                                                                    I   I  I
                                                                    I   I  I
        atcatgctcaacaccagtctccacaatgtccgggacaagcgggcctggagcgc
    199 -+---------+---------+---------+---------+---------+--------- 258
        tagtacgagttgtggtcagagagttaggtttacaggtttcggcccgttcggccccgaccctcgcg a.a.     I  M  L  N  T  S  L  H  N  P  N  V  R  D  K  P  G  L  E  R  -
```

FIG. 3B

```
                                              E
                                              c
               E  HM   B                      oAP        B          B
               a  as   p                      Ocs        Es  B      p  u
               e  ec   m                      1ep        cu  s      u  1
               I  II   I                      0I5        o3  p      1  0
                                              9II        N6  M      0
                                              III        II  I      I tttgtggccatgaaccggggcatcaacgagggcggggaccctgcctgaggagctgctcagg
259  --+---------+---------+---------+---------+---------+---------+-- 318
       aaacaccggtacttggccccgtagttgctcccgccccctggacgactcctcgacgagtcc B
                                                          s   u
                                                          p   3
                                                          B1  6
                                                          a2  I
                                                          n8  I
                                                          I6
                                                          II a.a.    F  V  A  M  N  R  G  I  N  E  G  G  D  L  P  E  E  L  L  R  -

```
319  aacctgtacgacagcatccgaatgagcccttcaagattcctgaggatgacgggaatgac
     -+---------+---------+---------+---------+---------+--------  378
     ttggacatgctgtcgtaggcttactcgggaagttctaaggactcctactgcccttactg a.a.  N  L  Y  D  S  I  R  N  E  P  F  K  I  P  E  D  D  G  N  D  -
                              EcoR7I
                              BsbI
                              Hsa
                              I
                              I 379  ctgacccacacctttcttcaaccggagggctggctcctgaagtctgggaggggc
     -+---------+---------+---------+---------+---------+--------  438
     gactgggtgtggaagaagttggcctggccctcccgaccgaggacttcgaccctccccg a.a.  L  T  H  F  F  N  P  D  R  E  G  W  L  L  K  L  G  G  G  -

439  cgggtgaagacgtggaagcggctggtttatcctcacagacaactgcctctactttt
     -+---------+---------+---------+---------+---------+--------  498
     gcccacttctgcacttcgccgaccaaataggagtgtctgttgacggagatgatgaaa
```

```
                                        A                      E       GB                            D
                                        c                      E       EEds                          r
                                        e                      c       aai i                         a
                                        I                      i       egIE                          I  I  I
                                        I                      I       IIII                          I  I  I
     cagctcatcaaagcctgcaaaactgagggcgacggccgagtggtggagggaaaccacatg  678
619 -+---------+---------+---------+---------+---------+---------+
     gtcgagtagtttcgacgtttgactcccgctgccggctcaccacctccctttggtgtac
                                                              //
a.a.  Q  L  I  K  A  C  K  T  E  A  D  G  R  V  V  E  G  N  H  M  -

B  B                          R                      R  B
                 s  s                          l                      e  s
                 a  t                          e                      e  e
                 W  Y                          A                      I  R
                 I  I                          I                      I  I
     gtgtaccggatctcggcccccacacaggaggagaaggacgagtggatcaagtccatccag  738
679 -+---------+---------+---------+---------+---------+---------+
     cacatggcctagagccggggtgtgtcctcctcttcctgctcacctagttcaggtaggtc a.a.  V  Y  R  I  S  A  P  T  Q  E  E  K  D  E  W  I  K  S  I  Q  -
```

FIG. 3F

```
739  gcggctgtgagtgtggaccccttctatgagatgctggcagcgagaagaagcggatttca  798
     -+---------+---------+---------+---------+---------+---------+-
     agccgacactcacacctggggaagatactctaagactgtcgctctcttcgcctaaagt a.a.    A  A  V  S  V  D  P  F  Y  E  M  L  A  A  R  K  K  R  I  S 799  gtcaagaagaagcaggagcagcccctgaccccctgcccccaactccattattattacgga  858
     -+---------+---------+---------+---------+---------+---------+-
     cagttcttcttcgtcctcgtcgggactgggggacggggttgaggtaataataatgcct a.a.    V  K  K  Q  E  Q  P  *  P  P  A  P  N  S  I  I  Y  Y  G
```

FIG. 3G

```
859  gctgccccgcctgggtggccggccctggggccgaccccctgggcctgtggatcctggttccctgt
     -+----+----+----+----+----+----+----+----+----+----+----+-  918
     cgacggggcggaccgccaccggcctgggccccgacccctggggactaggaccaagggaca a.a.      A  A  P  P  G  W  P  D  D  P  W  A  L  G  L  W  I  L  V  P  C  -

BamHI
                                    ApoI 919  ttggaaaattcaccacctctagctcctcactgttctttgtaattaacacgctgttggtaa
     -+----+----+----+----+----+----+----+----+----+----+----+-  978
     aaccttttaagtggtggagatcgaggagtgacaagaaacattaattgtgcgacaaccatt a.a.      L  E  N  S  P  P  L  A  P  H  C  S  L  *  L  T  R  C  W  *  -

AvaX
                                                                   DraI
                                                                   vh
                                                                   ao
                                                                   II
```

*FIG. 3H*

```
979  tcttattaattatttaaaaaaaaaaaaaaaaaaaaaaactcgag  1027
     -+----|----+----|----+----|----+----|----+-
     agaataattaataaatttttttttttttttttttttttgagctc a.a.  S  Y  *  L  F  K  K  K  K  K  K  K  T  R  -
```

FIG. 31

CYTHOHESIN-PH PEPTIDES THAT AFFECT THE ABILITY OF INTEGRINS TO ADHERE

The present invention relates to the use of cytohesin-PH peptides to influence the ability of integrins to adhere.

BACKGROUND OF THE INVENTION

T-Lymphocyte activation is achieved by coordinated binding of adhesion molecule receptors and signal receptors which are then expressed on the surface of T cells when these receptors bind to their complementary receptors on the antigen-presenting cell. Besides the T-cell receptors (TCRs) and MHC (major histocompatibility class) class I or II proteins, which are always involved in leukocyte activation, various types of coreceptors also are necessary, such as the integrins, and the CD2, CD4 and CD8 molecules. The functional interaction between the TCRs and the T-lymphocyte coreceptors is dynamic in nature, that is, only the binding of a TCR to its target molecule brings about enhanced binding of the coreceptors to their complementary receptors.

The integrins are a large family of cell surface molecules. These molecules are heterodimers that comprise pairs of α and β chains without disulfide linkages. Because there are several different α and β chains, differences in ligand specificity are achieved by different combinations of the α and β chains. The integrins are involved both in direct cell-cell interaction and in the binding of cells to the extracellular matrix.

Integrins that occur on non-activated lymphocytes are in a so-called "low-avidity state," which is converted very rapidly by T-cell activation into a transient so-called "high-avidity state." The mechanism of this so-called "inside-out signaling" has not yet been elucidated, however. Collins et al. *Curr. Opinion Imm.* 6: 385–393 (1994).

According to the affinity modulation model on T-cell activation, there is a conformational change in the integrins which first makes the high-affinity ligand binding site accessible to the ligand. Possible molecular events bringing about the conformational change which are currently suggested are covalent modification (for example, phosphorylation) or binding of activator or repressor molecules to the cytoplasmic domain of the integrin β subunit, but there is no experimental evidence in favor of a particular mechanism. Diamond and Springer, *Curr. Biol.* 4: 506–517 (1994).

Another type of signal protein is the hsec7hom (human SEC7 homolog) protein, which is mainly expressed in natural killer cells and cytotoxic T cells. This protein was thought to be the human homolog of the SEC7 protein from *S. cerevisiae*. However, because of the (i) great difference in the molecular weights of SEC7 and hsec7hom, (ii) the sequence similarity that is limited to a relatively short section, and (iii) the specific expression of hsec7hom, it is now thought that hsec7hom does not belong to the SEC7 protein family. See Liu and Pohaidak, *Biochimica et Biophysica Acta* 1132: 75–78 (1992)) For these reason, the hsec7hom protein will be referred to as "cytohesin-1."

Cytohesin-1 contains two regions which are homologous with domains of other proteins:

1. SEC7 domain: this domain contains about 200 amino acids and is only known to be found in a few other proteins. One of these proteins is the SEC7 protein, which is involved in secretion in yeasts. Another protein that possesses this domain is EMB30, which is involved in embryogenesis in Arabidopsis. Shevell et al., *Cell* 77: 1051–1062 (1994).

2. PH domain (Pleckstrin homology domain): this domain is about 100 (±25) amino acids long and has been found in a number of proteins, many of which play a part in the signal transduction. The three-dimensional structure of some PH domains has been elucidated. These domains are able to function as ligand-binding domains. Tsukada et al., *Proc. Nat'l Acad. Sci USA* 91: 11256–60 (1994). Although it has been shown that the heterotrimeric G proteins can interact with PH domains, no exact physiological function for PH domains has been previously found. Birney, *TIBS* 19: 349–353 (1994). Because the C-terminus of the PH domain has not been conclusively determined, larger amino acid sequences can be employed to ensure that the entire PH domain is present.

The PH domain is of major importance with regard to the present invention because of its ability to interact with the integrins.

The integrins are found on leukocyte surfaces and are involved in the inflammation process. Within minutes after receiving an inflammatory stimulus, the integrins acquire, through signal transduction pathway(s), the ability to attach to cell-surface and extracellular ligands. In some cases, the activation is transient, which means that the integrins quickly lose the ability to adhere. The dynamic cycling between adhesive and non-adhesive states endows a cell with the ability to rapidly regulate adhesion to ligands on apposing cell surfaces and matrices. This ability may be implicated in cell movement, which requires a rapid flux of adhesive interactions.

The function of integrin adhesion was initially documented in experiments that interfered with integrin function by using antibodies of peptide antagonists. The physiology of integrins has been assessed by the investigation of natural or induced genetic mutations of individual subunits. These mutations result in a variety of pathological sequelae.

Integrin-mediated adhesions has functional roles in a wide variety of biological and pathological settings, including hemostasis, inflammation, and tumor metastasis and development. For example, in primary hemostasis, platelet attachment to blood vessel walls, and aggregation at the site of injury are mediated by the integrins. Adhesion and signal transduction by integrins are essential elements of a sequence of intracellular interactions leading to antigen-specific activation of T-lymphocytes.

In inflammation, integrins mediate the critical attachment-strengthening step in the adhesion cascade, which permits leukocytes to move from the vasculature, across the endothelium lining blood vessels, and into the parenchyma. The subsequent migration of cells through the parenchyma depends upon the transient nature of integrin adhesiveness. This migration also may depend upon a sequence of attachment and detachment of ligand(s) by rapidly activated and inactivated integrin subpopulations, which are located and the leading and trailing edges of the migrating cells.

Because the vast array of functions performed by the integrins, these molecules are implicated in a large number of disease states. Accordingly, there is a need for methods of influencing the ability of integrins to adhere. This need is satisfied by the present invention.

SUMMARY OF THE INVENTION

It is an object of the present invention to provide methods of influencing the ability of integrins to adhere.

It is another object of the present invention to provide methods of influencing the ability of integrins to adhere by employing cytohesin-PH.

It is still another object of the present invention to administer proteins that contain the cytohesin-PH peptide to patients to treat diseases and otherwise improve the physical condition.

It is yet another object of the present invention to provide assays, including those to screen drugs, using proteins that contain the cytohesin-PH peptide.

In accomplishing these and other objects, there is provided, in accordance with one aspect of the invention, the use of a cytohesin-PH peptide, in particular as shown in FIG. 2 (SEQ ID NO: 12) or parts of the sequence shown therein, such as amino-acid positions 258 to 398, (residues 258 to 398 of SEQ ID NO: 12) to regulate the T-lymphocyte activation.

The invention furthermore relates to the use of a DNA coding for a cytohesin-PH peptide, in particular as shown in FIG. 2 (SEQ ID NO: 11) or parts of the sequence shown therein, such as nucleotide positions 841 to 1263, (bases 841 to 1263 of SEQ ID NO:11) for expression of the peptide.

The invention furthermore relates to the use of a DNA whose sequence is degenerate (often referred to as codon/anticodon wobble) with respect to the sequence of the DNA mentioned above in accordance with the nature of the genetic code.

The invention furthermore relates to the use of a DNA which hybridizes under stringent conditions with the DNA shown in FIG. 2 (SEQ ID NO: 11). Such DNAs include probes, which can be used to identify and/or isolate a gene or other nucleotide sequence. One type of DNA according to the invention would hybridize to the DNA of FIG. 2 (SEQ ID NO: 11) under highly stringent conditions.

The invention furthermore relates to vectors comprising a DNA described above and the use thereof for the expression of a cytohesin-PH peptide.

The invention furthermore relates to host cells comprising one of the vectors described above, and uses thereof.

The invention additionally relates to the use of a cytohesin-PH peptide described above for reducing or otherwise influencing inflammations, for improving wound healing, for suppressing the immune system, in particular in organ transplants, for preventing metastasis of hematopoietic tumors and for treating arteriosclerosis.

The invention furthermore relates to a pharmaceutical comprising a cytohesin-PH peptide and a physiologically acceptable vehicle and, where appropriate, suitable additives and/or ancillary substances.

The invention furthermore relates to an assay system with relevance for therapeutic use comprising the cytohesin-PH domain, preferably a drug screening assay system.

The invention furthermore relates to a cytohesin-2 peptide having the amino-acid sequence shown in FIG. 1B (SEQ ID NO: 10). The invention additionally relates to the use of a cytohesin-2 peptide having the amino-acid sequence encoded by the cts 18.1-cDNA (SEQ ID NO: 14) to regulate T-lymphocyte activation. The invention additionally relates to a DNA coding for a cytohesin-2 peptide or parts thereof. A sample of the cts 18.1 cDNA has been deposited at the DSMZ-Deutsche Sammlung von Mikroorganismen und Zellkulturen GmbH, Mascheroder Weg 1b, D-38124 Braunschweig, Germany. The deposit has been assigned accession number DSM 13656.

The invention furthermore relates to a DNA whose sequence is degenerate with respect to the sequence of the DNA mentioned above in accordance with the nature of the genetic code. Degeneracy is often referred to as codon/anticodon wobble, and is discussed in Watson et al., MOLECULAR BIOLOGY OF THE GENE (4th ed. 1987) at 437–43. Also within the scope of the invention are so-called "polyamide" or "peptide" nucleic acids ("PNAs"), which replace the (deoxy) ribose phosphate backbone with an achiral polyamide backbone or the like. See Nielsen et al., *Science* 254: 1497–54 (1991).

The invention furthermore relates to the use of a DNA coding for a cytohesin-2 peptide for expression thereof. The invention furthermore relates to the use of a cytohesin-2 peptide as shown in FIG. 1B (SEQ ID NO: 10) for influencing inflammations, for improving wound healing, for suppressing the immune system (in particular in organ transplants), for preventing metastasis of hematopoietic tumors and for treating arteriosclerosis.

The invention furthermore relates to a pharmaceutical comprising a cytohesin-2 peptide and a physiologically acceptable vehicle and, where appropriate, suitable additives and ancillary substances.

The invention furthermore relates to a process for the preparation of a cytohesin-PH peptide described above, which comprises:

(a) cultivating a host cell containing DNA encoding a cytohesin-PH peptide, and (b) isolating the cytohesin-PH peptide.

Another aspect of the invention includes methods of regulating T-lymphocyte adhesion in a patient, comprising the step of administering to the patient an amount of a cytohesin-PH peptide. The cytohesin-PH peptide has an amino-acid sequence as shown in FIG. 2 (SEQ ID NO: 12), such as shown at positions 258 to 398 of FIG. 2 (residues 258 to 398 of SEQ ID NO:12). The method can be used to treat inflammation, improve wound healing, regulate the immune system (including suppression for organ transplant patients), treat hematopoietic tumors, and/or treat arteriosclerosis.

In accordance with still another aspect of the invention, there are provided methods of making a cytohesin-PH peptide for regulating T-lymphocyte adhesion, comprising the step of expressing a polynucleotide that hybridizes under stringent conditions with the DNA shown in FIG. 2 (SEQ ID NO: 11). The method can employ the sequence set forth at FIG. 2 (SEQ ID NO: 11), or portions thereof, such as the sequence set forth at positions 841 to 1263 of FIG. 2 (bases 841 to 1263 of SEQ ID NO: 12).

In accordance with yet another aspect of the invention, there are provided a cytohesin-2 peptides having the amino-acid sequence shown in FIG. 1B (SEQ ID NO: 10).

In accordance with yet a further aspect of the invention, there are provided pharmaceutical compositions comprising a cytohesin-PH peptide and/or a cytohesin-2 peptide along with a physiologically acceptable carrier. The pharmaceutical preparations can further comprise suitable additives and ancillary substances. Additionally, the pharmaceutical composition can be composed of cytohesin-PH and/or cytohesin-2 peptides as the only ingredient(s) that affect integrin adhesion.

In accordance with still a further aspect of the present invention, there are provided polynucleotides encoding a cytohesin-PH peptide and/or a cytohesin-2 peptide. The polynucleotides can hybridize under stringent conditions with the DNA shown in FIG. 2 (SEQ ID NO:11). The polynucleotides encoding the cytohesin-PH peptide can comprise the sequence set forth at FIG. 2 (SEQ ID NO: 11), or portions thereof, such as positions 841 to 1263 of FIG. 2 (bases 841 to 1263 of SEQ ID NO:11).

In accordance with still a further aspect of the present invention, there are provided assay kits comprising a cytohesin-PH peptide or as cytohesin-PH peptide. The assays kits can be used for drug screening, among other things.

In accordance with yet a further aspect of the present invention, there are provided methods of evaluating the effects of compounds, comprising the steps of contacting a compound with a cytohesin-PH peptide and determining the effects of the compound on the activity of cytohesin-PH. One type of assay would include cytohesin-PH or the test compound, wherein only one is bound to an insoluble matrix, such as SEPHAROSE. The other is labelled (radioactively, enzymatically, magnetically, or other appropriate labels), and a direct binding assay is conducted. This assay is capable of identifying compounds that bind to, and thus possibly block or inhibit, cytohesin-PH. Compounds that bind cytohesin-PH should then be tested with the cellular assays, described below.

Methods for evaluating the effects of compounds with cytohesin-PH also are provided. Such methods include cellular assays. A cellular assay could comprise the steps of: growing a test group and a control group cells that possess the ability to adhere to a substrate (such as a culture dish coated with ICAM-1-Rg or the like), wherein the test group is grown in the presence of a test compound and the control group is grown in the absence of a test compound; inducing the expression of cytohesin-PH in the test cells and the control cells; and comparing the extent of adhesion loss by the test group and the control group. In a valid test, the control group cells would lose adhesive capabilities. If the cells of the test group lose adhesive capabilities to a lower degree, the test compound interferes or blocks the anti-adhesive properties of cytohesin-PH.

The invention also includes the experimental steps which are explained by way of example are listed hereinafter:

1) Preparation of the CD18 cyt bait construct;
2) Preparation of the yeast expression bank;
3) Screening with the two-hybrid system;
4) Test of the binding specificity in yeast;
5) Preparation of the fusion constructs for testing the function of cytohesin-1 in vivo;
6) Function assay for cytohesin-1 and the subdomains
7) Preparation of the ICAM-Rg fusion protein; and
8) Cytohesin-PH domain-specific functional inhibition of β2 integrins.

The present invention encompasses biotechnology inventions, including biotechnological processes.

Still other aspects of the invention will be apparent to the skilled person in view of the teachings contained herein.

BRIEF DESCRIPTION OF THE FIGURES

FIGS. 1A and B depict the cytohesin-PH peptide. FIG. 1A is a schematic diagram of the cytohesin-PH peptide as in is found in cytohesin-1 (encoded by B2-1) and cytohesin-2 (encoded by cts18.1). FIG. 1B depicts and compares the amino acid sequences of cytohesin-1 (SEQ ID NO: 9) and cytohesin-2 (SEQ ID NO: 10). The amino acid upper sequence (SEQ ID NO: 9) is the cytohesin-1 amino acid sequence starting at residue 136, and the lower sequence (SEQ ID NO: 10) is the cytohesin-2 amino acid sequence starting at residue 1. Solid lines (|) indicate matches; single dots (.) indicate semiconservative changes; and double dots (:) indicate conservative changes.

FIGS. 2A–2Y depict both DNA stands of the cytohesin-1 cDNA (SEQ ID NO:11 with appropriate numbering) and the amino-acid sequence of the cytohesin-1 protein derived from the cDNA ( SEQ ID NO:12 also with appropriate numbering). The stop codon is shown by an asterisk.

FIGS. 3A–3I depict both DNA strands of the cytohesin-2 cDNA from cts 18.1 (SEQ ID NO: 13 with appropriate numbering) and the amino-acid sequence of the cytohesin-2 protein derived from the cDNA (SEQ ID NO:14 also with appropriate numbering).

FIG. 4A schematically depicts ICAM-1-Rg, clg-cytohesin-1, clg-SEC7 and clg-PH. FIG. 4B depicts the expression of cytohesin-1 fusion protein in J32 cells (lane 1 is clg control, lane 2 is clg-cytohesin-l, lane 3 is clg-sec7, and lane 4 is cIg-PH). FIG. 4C depicts data from an adhesion assay of the above fusion proteins using unstimulated cells and OKT3 stimulated cells.

DETAILED DESCRIPTION OF PREFERRED EMBODIMENTS

Figure 4A:
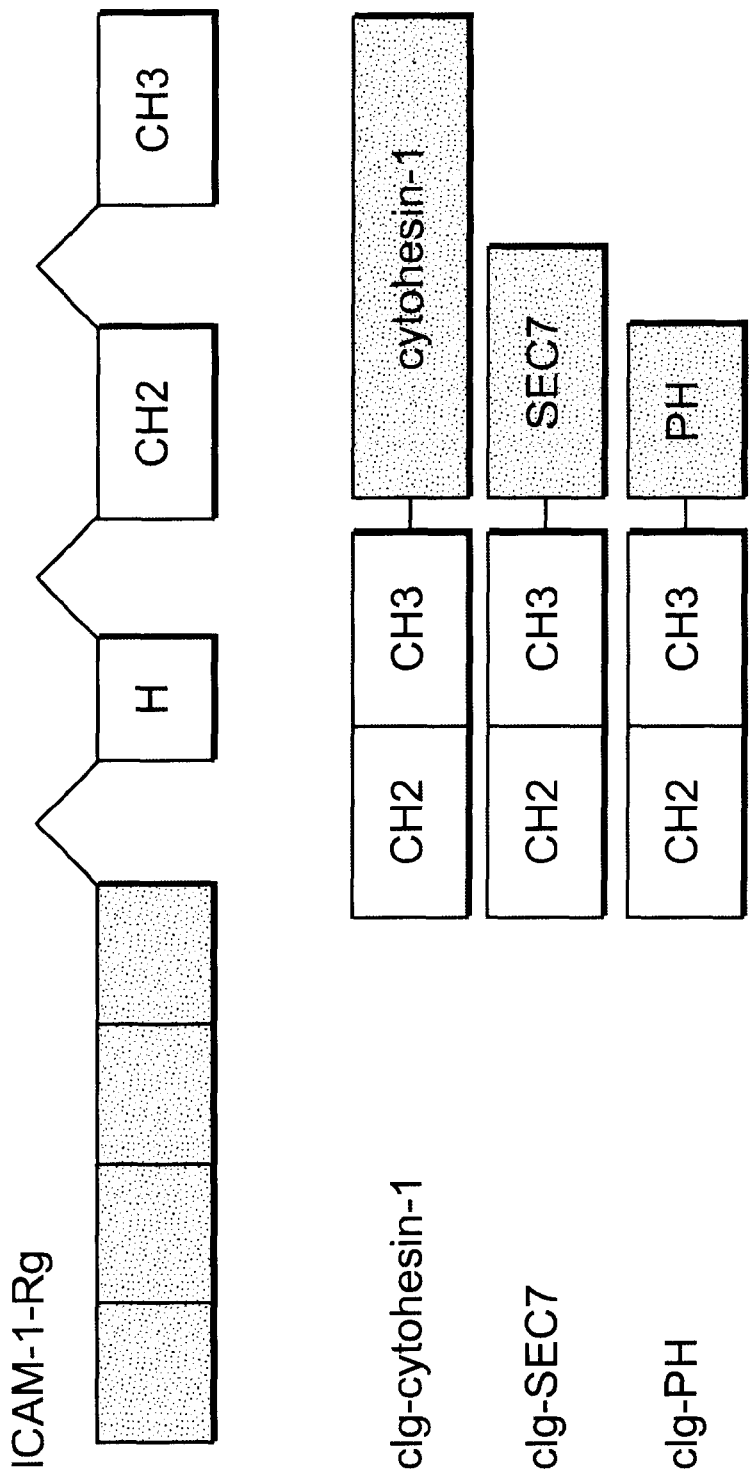
FIGS. 4A–C concern the influence of full-length cytohesin-1, PH and SEC7 domain fusion proteins on the binding of J32 cells to ICAM-1-Rg.

The present invention satisfies the need to intervene in the physiological occurrence in all biological processes in which modulation of avidity is involved. More specifically, the avidity pertaining to the present invention concerns the adhesive properties of the integrins and the involvement of the integrins in disease states and other biological conditions, including abnormal conditions. Examples of the biological processes involving integrins include wound healing, development of organs, and the wide range of functions of the immune system. The present invention relates to polypeptides that interact directly and/or functionally with the cytoplasmic domain of the β2 subunit of the integrins (β2cyt) and the like. These polypeptides can be used in a variety of contexts, including treatment of hemostatic, inflammatory and cancerous conditions.

Polypeptides according to the invention were discovered by using the two hybrid system, also referred to as the interaction trap (Gyuris et al., *Cell* 75: 791–803 (1993); Fields and Sternglanz, *Trends in Genetics* 10: 286–92 (1994). For this purpose, the entire cytoplasmic domain of the β2 integrin subunit (β2cyt) was fused, exactly as described in the literature (Kishimoto et al., Cell. 48: 681–690, 1987), to a lex A binding domain in order to act as "bait". Because β2 integrins are expressed specifically in cells of hematopoietic origin, a yeast expression bank with the cDNA from Jurkat cells (obtained from T-cell tumors) was used for the screening.

The boundaries of the PH-domain has not been conclusively determined yet. Accordingly, fragments that are larger than 100 amino acids long (for example, about 140 residues, such as residues 258 to 398 of FIG. 2, residues 258 to 398 of SEQ ID NO: 12) can be employed in situations where the skilled person wants to reasonably ensure that the entire domain is present. FIG. 2 depicts both DNA strands of the cytohesin-1 cDNA (SEQ ID NO: 11), and identifies restriction sites. This DNA can be restricted by:

| ACC1  | ACI1   | AFL3  | AHA2   | ALU1  | ALW1  | ALWN1 |
|-------|--------|-------|--------|-------|-------|-------|
| APA1  | APAL1  | APO1  | AVA1   | AVA2  | AVR2  | BAL1  |
| BAMH1 | BAN1   | BAN2  | BBS1   | BBV1  | BGL1  | BGL2  |
| BPM1  | BSA1   | BSAB1 | BSAW1  | BSG1  | BSIE1 | BSL1  |
| BSM1  | BSMA1  | BSMF1 | BSP12  | BSPM1 | BSPE1 | BSR1  |
| BSRB1 | BSRD1  | BSTN1 | BSTU1  | BSTY1 | CFR10 | DDE1  |
| DRA1  | DRA2   | DRA3  | DRD1   | EAE1  | EAM1  | EAR1  |
| ECO57 | ECOK   | ECON1 | ESP3   | FOK1  | FNU4H | HAE2  |
| HAE3  | HGA1   | HGIA1 | HHA1   | HINC2 | HINF1 | HPA2  |
| HPH1  | MAE1   | MAE2  | MAE3   | MBO2  | MNL1  | MSE1  |
| MSL1  | NCI1   | NCO1  | NLA3   | NLA4  | NSI1  | NSPB2 |
| NSPH1 | PLE1   | PPUM1 | PST1   | PVU2  | SAC1  | SAC2  |
| SAP1  | SAU3A  | SAU96 | SCRF1  | SEC1  | SEXA1 | SFAN1 |
| SFC1  | SFI1   | SMA1  | SPH1   | SRF1  | SSE1  | STU1  |
| STY1  | TAQ1   | TFI1  | TSP5   | XBA1  | XCA1  | XCM1  |
| Enzymes that do not cut: ||||||||
| AAT2  | AFL2   | AGE1  | ASC1   | ASE1  | BCG1  | BCL1  |
| BSAA1 | BSIW1  | BSPH1 | BSRG1  | BSSH2 | BSTB1 | BSTE2 |
| BSTX1 | BSU36  | CLA1  | EAG1   | ECO47 | ECO81 | ECOR1 |
| ECORV | ESP1   | FSP1  | HIND3  | HPA1  | KPN1  | MLU1  |
| MUN1  | NAE1   | NAR1  | NDE1   | NHE1  | NOT1  | NRU1  |
| PAC1  | PFLM1  | PME1  | PML1   | PSP14 | PVU1  | RSA1  |
| RSR2  | SAL1   | SCA1  | SGRA1  | SNAB1 | SPE1  | SSP1  |
| SWA1  | TTH1   | XHO1  | XMN1   |       |       |       |

A cDNA (cts 18.1) has now been identified and exhibits similarity with the previously known B2-1 cDNA (Liu and Pohajdak) which codes for the cytohesin-1 described above. The function of cytohesin-1 in nature remains undetermined.

DNA sequences also are part of the invention. For example, the invention pertains to DNA, and uses thereof, which hybridize under stringent conditions with the DNA shown in FIG. 2 (SEQ ID NO:11). Such DNAs include probes, which can be used to identify and/or isolate a gene or other nucleotide sequence. One type of DNA according to the invention would hybridize to the DNA of FIG. 2 (SEQ ID NO: 11). A under highly stringent conditions. Such conditions include the use of 6×SSC or 6×SSPE, 0.5% SDS, 100 μg/ml denatured and fragmented salmon sperm DNA at 68° C. Other conditions, including those that create higher or lower stringency, also are within the invention.

The gene product of the cDNA cts 18.1 is referred to as cytohesin-2. See FIG. 3 (SEQ ID NO: 13). The DNA of FIG. 3 (SEQ ID NO: 13), can be cleaved by:

| AceIII   | AflIII   | ApoI    | AvaI     | BamHI   | BanII  |
|----------|----------|---------|----------|---------|--------|
| BbsI     | BglI     | BpmI    | Bpu10I   | BsaAI   | BsaWI  |
| BsbI     | BseRI    | BsgI    | BsiEI    | sp1286I | BspMI  |
| BstYI    | Bsu3GI   | DraI    | DraIII   | DrdII   | DsaI   |
| EaeI     | EagI     | EciI    | Eco47III | Eco57I  | EcoNI  |
| EcoO109I | GdiII    | HaeI    | HaeII    | Hin4I   | MscI   |
| PmlI     | Psp5II   | RleAI   | RsrI1    | StuI    | StyI   |
| TaqII    | Tth111II | VspI    | XhoI     |         |        |
| Enzymes that do not cut: ||||||
| AatII    | AccI     | AflII   | AhdI     | AlwNI   | ApaI   |
| ApaBI    | ApaLI    | AscI    | AvrII    | BaeI    | BanI   |
| Bce83I   | BcgI     | BcgJ    | BclI     | BglII   | BmgI   |
| Bpu1102I | BsaI     | BsaBI   | BsaHI    | BsaXI   |        |
| BsiHKAI  | BsmI     | BsmBI   | Bsp24I   | Bsp24I  | BspEI  |
| BspGI    | BspLU11I | BsrBI   | BsrDI    | BsrFI   | BsrGI  |
| BssHII   | BssSI    | Bst1107I| BstEII   | BstXI   | ClaI   |
| DrdI     | EarI     | EcoRI   | EcoRV    | FseI    | FspI   |
| HgiEII   | HincII   | HindIII | HpaI     | KpnI    | MluI   |
| MmeI     | MslI     | MspA1I  | MunI     | NarI    | NcoI   |
| NdeI     | NgoAIV   | NheI    | NotI     | NruI    | NsiI   |
| NspI     | NspV     | PacI    | Pfl1108I | PflMI   | PinAI  |
| PmeI     | PshAI    | Psp1406I| PstI     | PvuI    | PvuII  |
| RcaI     | SacI     | SacII   | SalI     | SanDI   | SapI   |
| ScaI     | SexAI    | SfcI    | SfiI     | SgfI    | SgrAI  |
| SmaI     | SnaBI    | SpeI    | SphI     | SrfI    |        |
| Sse8387I | Sse8647I | SspI    | SunI     | SwaI    |        |
| Tth111I  | XbaI     | XcmI    | XmnI     |         |        |

Because of the similarity of cytohesin-1 and cytohesin-2 (88% identity, 9% conserved amino-acid exchanges), the two proteins may have a similar or identical function. Moreover, because of the similarity of cDNAs B2-1 and cts 18.1, hybridization of the two molecules is possible under stringent conditions by methods well known to the skilled worker.

It has now been found, surprisingly, that a peptide with the amino-acid sequence of the PH domain of cytohesin-1 or cytohesin-2, in particular cytohesin-1 as shown in FIG. 2 (SEQ ID NO:12), can be used to regulate T-lymphocyte activation. The peptide is referred to as "cytohesin-PH peptide."

Also suitable for use pursuant to the present invention are fragments of the cytohesin-PH and cytohesin-2 peptides and variants of these peptides, such as analogs, homologs, derivatives, muteins and mimetics of the natural molecule, which retain the ability to effect the benefits described above.

Fragments of the peptides refers to portions of the amino acid sequence of the cytohesin-PH or cytohesin-2 polypeptide. These fragments can be generated directly from the peptides themselves by chemical cleavage, by proteolytic enzyme digestion, or by combinations thereof. Additionally, such fragments can be created by recombinant techniques employing genomic or cDNA cloning methods. Furthermore, methods of synthesizing polypeptides directly from amino acid residues also exist.

The variants (often referred to as analogs, homologues, derivatives, muteins and mimetics) of the cytohesin-PH and cytohesin-2 peptides can be produced by these and other methods. For example, amino acid substitutions can be undertaken in the peptides.

Amino acid residues can be categorized in terms of pH, hydrophilicity/hydrophobicity, and other characteristics. Typically, substitutions are undertaken in a manner to take these characteristics into consideration, and thus amino acids with similar characteristics are employed in the substitutions. The more similar amino acids are to one another, the more "conservative" a substitution is deemed to be. For example, illustrative conservative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine. Other substitutions also can be employed according to the invention.

Site-specific and region-directed mutagenesis techniques can be employed to effect changes in the peptides employed according to the invention. See CURRENT PROTOCOLS IN MOLECULAR BIOLOGY vol. 1, ch. 8 (Ausubel et al. eds., J. Wiley & Sons 1989 & Supp. 1990–93); PROTEIN ENGINEERING (Oxender & Fox eds., A. Liss, Inc. 1987).

In addition, linker-scanning and PCR-mediated techniques can be employed for mutagenesis. See PCR TECHNOLOGY (Erlich ed., Stockton Press 1989); CURRENT PROTOCOLS IN MOLECULAR BIOLOGY, vols. 1 & 2, supra.

Non-peptide compounds that mimic the binding and function of a peptide ("mimetics") also are contemplated within the invention, and can be produced by the approach outlined in Saragovi et al., Science 253: 792–95 (1991). Mimetics are peptide-containing molecules which mimic elements of protein secondary structure. See, for example, Johnson et al., "Peptide Turn Mimetics" in BIOTECHNOLOGY AND PHARMACY, Pezzuto et al., Eds., (Chapman and Hall, New York, 1993). The underlying rationale behind the use of peptide mimetics is that the peptide backbone of proteins exists chiefly to orient amino acid side chains in such a way as to facilitate molecular interactions For the purposes of the present invention, appropriate mimetics can be considered to be the equivalent of the cytohesin peptides themselves.

Protein sequencing, structure and modeling approaches for use with any of the above techniques are disclosed in PROTEIN ENGINEERING, loc. cit. and CURRENT PROTOCOLS IN MOLECULAR BIOLOGY, vols. 1 & 2, supra.

The cytohesin-PH peptide, or peptides containing a PH peptide (e.g., cytohesin-2, cytohesin-1 and the like), can be used to make pharmaceutical compositions that have beneficial effects. The pharmaceutical compositions can be used to treat a variety of disease states or other abnormalities where modifying or influencing the ability of the integrins to adhere will be useful. For example, the pharmaceutical compositions can be used to treat inflammation, hematopoietic tumors, and/or arteriosclerosis. The term "treat" in its various grammatical forms in relation to the present invention refers to preventing, curing, reversing, attenuating, alleviating, minimizing, suppressing or halting the deleterious effects of a disease state or progression. The pharmaceutical compositions are contemplated to be administered to "patients," which typically are animal subjects, such as humans, who are in need or will be in need of the beneficial effects of the pharmaceutical compositions.

The pharmaceutical compositions also can be used to improve wound healing (another beneficial effect). Moreover, these compositions can be used to regulate the immune system (still another beneficial effect). The term "regulate" in its various grammatical forms in relation to the present invention refers to a modulation, alteration or change (increase or decrease) in the rate, manner and/or result of an activity of a biological system. For example, the pharmaceutical compositions can be used to suppress the immune system of organ transplant patients to prevent rejection. The suppression would be a type of regulation of the immune system.

The pharmaceutical compositions can be used, for example, in the form of pharmaceutical products which can be administered orally, for example, in the form of tablets, coated tablets, hard or soft gelatin capsules, solutions, emulsions or suspensions. These compositions also can be administered rectally, for example, in the form of suppositories, or parenterally, for example, in the form of injection solutions. To produce pharmaceutical products, these compounds can be processed in therapeutically inert organic and inorganic vehicles. Examples of such vehicles for tablets, coated tablets and hard gelatin capsules are lactose, corn starch or derivatives thereof, talc and stearic acid or salts thereof. Suitable vehicles for producing solutions are water, polyols, sucrose, invert sugar and glucose. Vehicles suitable for injection solutions are water, alcohols, polyols, glycerol and vegetable oils. Vehicles suitable for suppositories are vegetable and hardened oils, waxes, fats and semiliquid polyols. The pharmaceutical products may also contain preservatives, solvents, stabilizers, wetting agents, emulsifiers, sweeteners, colorants, flavorings, salts to alter the osmotic pressure, buffers, coating agents, antioxidants and, where appropriate, other therapeutic active substances. Other suitable carriers and/or ingredients are disclosed in REMINGTON'S PHARMACEUTICAL SCIENCES, 15th Ed. Easton: Mack Publishing Co. (1975); THE NATIONAL FORMULARY XIV., 14th Ed. Washington: American Pharmaceutical Association (1975); GOODMAN AND GILMAN'S THE PHARMACOLOGICAL BASIS FOR THERAPEUTICS (7th ed.).

Oral administration and injections are suitable administration routes. For injection, the cytohesin-PH peptides are formulated in a liquid solution, including physiologically acceptable buffers such as Hank's solution or Ringer's solution. The cytohesin-PH peptides may, however, also be formulated in solid form and be dissolved or suspended before use.

Dosages for systematic administration include about 0.01 mg/kg to about 50 mg/kg of body weight per day. Other dosaging and administration regimens will become apparent the person of skill in the art in view of the disclosure contained herein. Disease conditions and symptoms that would prompt administration of cytohesin-PH polypeptide (s) are apparent to the person of skill in the art in view of the teachings contained herein.

The invention is further described by the following examples, which do not limit the invention in any manner.

EXAMPLE 1

Preparation of the CD18 cyt Bait Construct

```
cgc ggg acg cgt gct ctg atc          (SEQ ID NO:1)
                                      (CD18 cyt for)
cac ctg agc cgc ggg gcg gcc gct tta act           (SEQ ID NO:2)
                                      (CD18 cyt rev)
ctc agc aaa ctt ggg
``` were used to amplify the cytoplasmic domain of CD18 from the full-length version of a cDNA clone of CD18 (Brian Seed, communication, corresponds to the sequence CD18 in Kishimoto et al., Cell 48, 681–690 (1987)) by PCR. The PCR DNA was digested with the restriction enzymes MluI and NotI, and the product was inserted into the vector pLex202 (Gyuris et al., Cell 75: 791–803 (1993)), which had been prepared by conventional methods of molecular biology. The sequence identity was verified by double-stranded sequencing. The resulting construct was called lex 202-cd18.

EXAMPLE 2

Preparation of the Yeast Expression Bank

Poly-A RNA was purified as described by Ausubel et al., CURRENT PROTOCOLS IN MOLECULAR BIOLOGY, Wiley Interscience, New York, 1987, from Jurkat E6 cells (ATCC TIB-152) and subjected to reverse transcription in vitro. The double-stranded cDNA was provided with EcoRI adapters, digested with XhoI and ligated into the vector pJG4-5 which had been EcoRI-XhoI digested. The bacterial strain MC1061 was then transformed with ligation mixture. Both the vector pJG4-5 and the bacterial strain MC1061 are disclosed in Gyuris et al. (1993). Initial amplification of the library produced 4×10⁶ recombinant clones. The bacterial cells were then lysed, and the double-stranded plasmid DNA was prepared as library stock (Ausubel et al., 1987).

EXAMPLE 3

Screening with the Two-hybrid System

The lex202-cd18 construct from EXAMPLE 1 was transformed by LiCl transformation (Ausubel et al., 1987) into the yeast strain EG048JK103 (Gyuris et al., 1993). The strain EG048JK103CD18 produced in this way was made competent for the library transformation via the LiCl method. Fifty micrograms of the library were transformed into these competent cells, which finally resulted in about 900,000 independent recombinant yeast clones on URA-HIS-TRP media. Aliquots of this yeast library (20×10⁶ cells) were plated out on URA(-)HIS(-)TRP(-)LEU(-)XGAL indicator plates, and positive clones (blue) were selected. Then plasmid DNA was prepared from the yeast cells (Ausubel et al., 1987) and subjected to double-stranded sequencing. This manipulation resulted in cDNA pJG4-5cts18.1, abbreviated to cts18.1., which is 97% homologous at the protein level with hsec7hom (Accession #:Genbank M85169), hsec7hom is called "cytohesin-1." The cDNA for cytohesin-1 can be referred to as B2-1 cDNA (Liu and Pohajdak, 1992). The product of cts18.1 is called cytohesin-2 (see FIG. 1B (SEQ ID NO: 10)).

A Jurkat cDNA library containing 4×10⁶ clones was produced using the yeast expression vector pJG4-5. An aliquot of the library was used to transform a yeast which had previously been transformed with a LexA–CD18 fusion protein expression plasmid. The resulting 8×10⁵ primary colonies were tested for interaction with the cytoplasmic domain of CD18.

EXAMPLE 4

Mapping of Cytohesin Interaction Domains

The cytohesin interaction domain with respect to CD18 cyt was mapped in yeast. The sequence cts18.1 and 2 PCR fragments which contained the SEC7 and PH domains of cytohesin-1 were cloned into the yeast expression vector PJG4-5. The constructs were introduced into yeast cells which had been plated on a media containing X-GAL, which is a color indicator. A blue color indicates an interaction between the fusion proteins. X-Gal as an indicator.

It was found that the SEC7 domain reproducibly interacted with CD18, whereas no interaction of CD18 could be detected with the PH-domain. The results are set forth in Table 1 below.

TABLE 1

| Constructs | CD 18 cyt |
| --- | --- |
| (a) vector PJG 4-5 alone (a negative control) | white |
| (b) PJG 4-5 (cts 18.1) | light blue |
| (c) PJG 4-5 (cytohesin-1 PH domain) | white |
| (d) PJG 4-5 (cytohesin-1 SEC 7 domain) | blue |

Because the PH domain dramatically interferes with β2-integrin function but does not bind to CD18 in yeast, as shown in Table 1 above, this domain appears to couple elements of the "inside-out" signaling pathways of the integrins.

EXAMPLE 5

Test of the Binding Specificity in Yeast pJG4-5cts18.1 was transformed into yeast EG048JK103 (see EXAMPLE 3) and the strain EG048JK103cts18.1 resulting therefrom was made competent for the test of binding specificity (Ausubel et al., 1987). These competent yeast cells were transformed with various lex202 constructs which had been prepared in an analogous manner to the CD18 bait construct (lex202-CD 29b, -CD2, -CD4, -CD8, Idlreceptor, -HIV-rev, -HIV-tat, -fyn, -syk, -ZAP-70). The yeast cells were plated out on URA(-), HIS (-), TRP(-) media, and positive clones were tested on URA(-)HIS(-)TRP (-)LEU(-)XGAL indicator media. The test criterion used was the blue coloration of the yeast cells.

The constructs were introduced into yeast cells which had been plated out on medium containing X-GAL. The interaction thus became visible due to the "color phenotype" of the corresponding yeasts. A blue color indicates an interaction between the fusion proteins.

The results are summarized in Table 2 below.

TABLE 2

| plex202 derivatives | pJG4-5 derivatives cytohesin1-SEC7 |
| --- | --- |
| lex-CD18cyt | blue |
| lex-CD29cyt | white |
| lex-CD2cyt | white |
| lex-CD4cyt | white |
| lex-CD8cyt | white |
| lex-Idlrcyt | white |
| lex-rev | white |
| lex-tat | white |
| lex-fyn | white |
| lex-syk | white |
| lex-ZAP70 | white |

Table 2 depicts the specificity of the interaction between CD18 cyt and cts 18.1. The clone cts 18.1 was transformed into yeast cells which already contained an expression construct encoding the $\beta_2$ cytoplasmic domain, or several other transmembrane cytoplasmic domains (-cyt), including the $\beta_1$ integrin cytoplasmic domain (CD29 cyt), and some control proteins.

EXAMPLE 6

Figure 6:
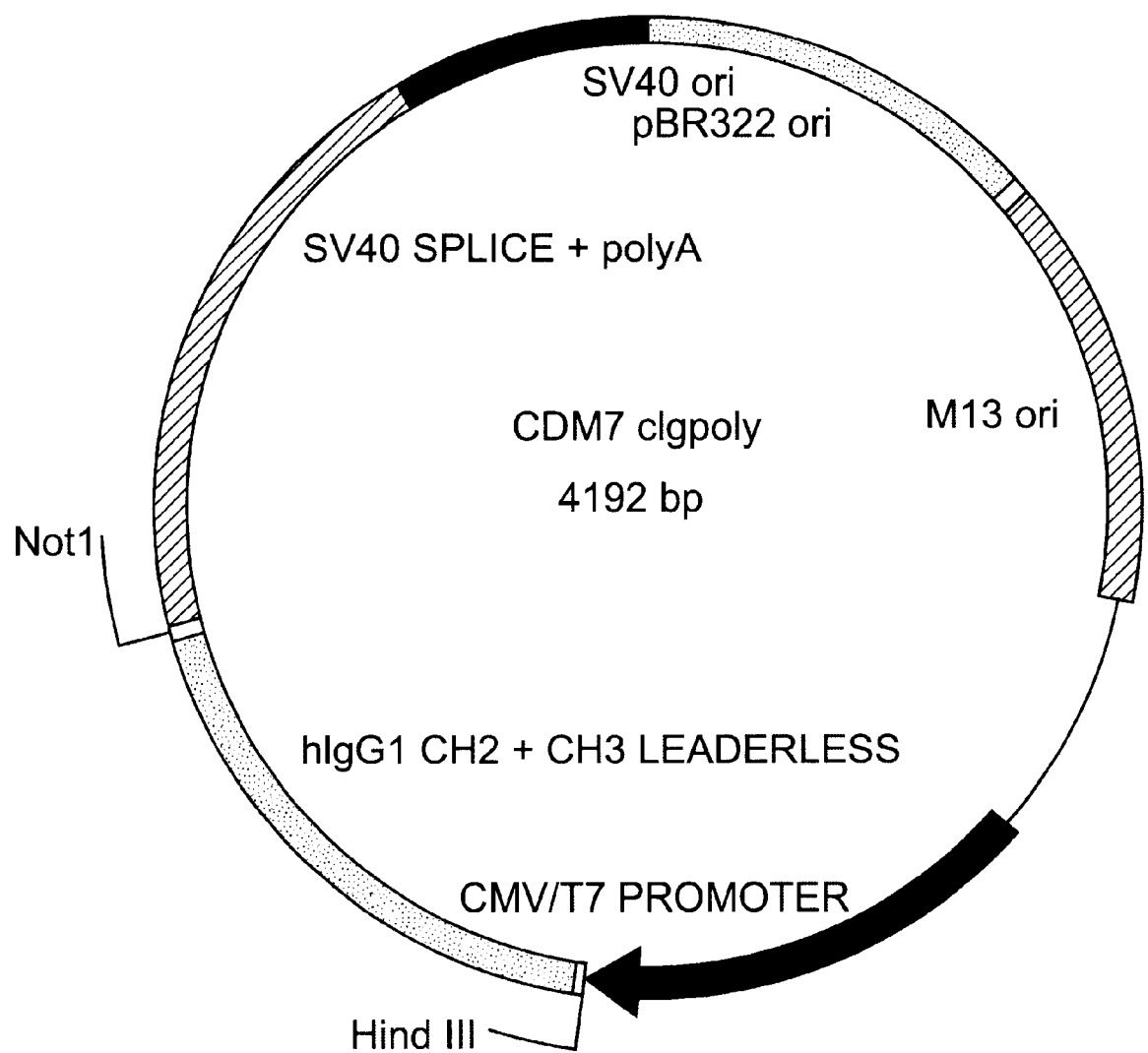
FIG. 6 is a schematic map of the vector CDM7cIgpoly.

Preparation of the Fusion Constructs to Test the Function of Cytohesin-1 In vivo Cytohesin-1 was amplified with the aid of the primers from a natural killer cell library, cloned via the restriction cleavage sites MluI and NotI into the vector pCDM7cIgpoly (see FIG. 6) and sequenced.

Primers

```
cgc ggg acg cgt atg gag         (SEQ ID NO:3)
                                (hsec7hom mlu)

gag gac gac agc tac gtt ccc cgc ggg gcg gcc gct tta gtg     (SEQ ID NO:4)
                                (hsec7hom not rev)

tcg ctt cgt gga gga gac ctt
```

The sequences which encode the PH and SEC7 subdomains were PCR-amplified from the cytohesin-1 sequence, and inserted into pCDM7cIgpoly, in an analogous manner.

Primers

```
gcg ggg acg cgt acc atg gct    (sec7 mlu nco for)(SEQ ID NO:6)

aat qaa att qaa aac ctg gcg ggg gcg gcc gct tta gaa    (sec7 not rev)    (SEQ ID NO:6)

agt gtg agt gag gtc att ccc cgc ggg acg cgt acc atg ggt    (ph mlu ncofor)   (SEQ ID NO:7)

ttc aat cca gac cga gaa ggc tgg cgc ggg gcg gcc gct tta gtg    (hsec7hom not rev)(SEQ ID NO:8)

tcg ctt cgt gga gga gac ctt
```

The construct for expression of ICAM-1 Rg was prepared in an analogous manner except that, in this case, the expression cassette is used to express a secreted immunoglobulin fusion construct. Preparation of the secreted Ig cassette is described in Walz et al. *Science* 250: 1132–35 (1990).

EXAMPLE 7

Function Assay of Cytohesin-1 and the Subdomains

The cDNA segments which code for cytohesin-1 and the particular subdomains were inserted together with the clg cassette into the vaccinia expression vector ptkg. Kolanus et al., *Cell* 74: 171–83 (1993). These vectors were transfected into CV-1-(ATCC70-CCL) cells which had been infected with wild-type vaccinia virus (WR). Recombinant viruses were obtained by gpt selection and amplified on CV-1 cells. For each of the values in the experiments, $5 \times 10^6$ Jurkat J32 (Tadmorei et al., *J. Immunol.* 136(4), 1155–60 (1986)) cells were infected with 100 µl of virus stock, in each case, whose titer had been at least $5 \times 10^7$ pfu/ml, and subsequently incubated in RPMI/10% FCS for 4 hours. The cells were then spun down and incubated in the presence or absence of a concentration of 3 mg/ml OKT3 antibody (purified from hybridoma supernatants, origin of the hybridoma: ATCC CRL-8001) at room temperature for 5 minutes. The suspension was pipetted into cell culture dishes (Falcon® 1008) coated with ICAM-1-Rg and incubated for a further 10 minutes. After washing with medium three times, the bound cells were fixed and counted under the microscope.

Figure 4B:
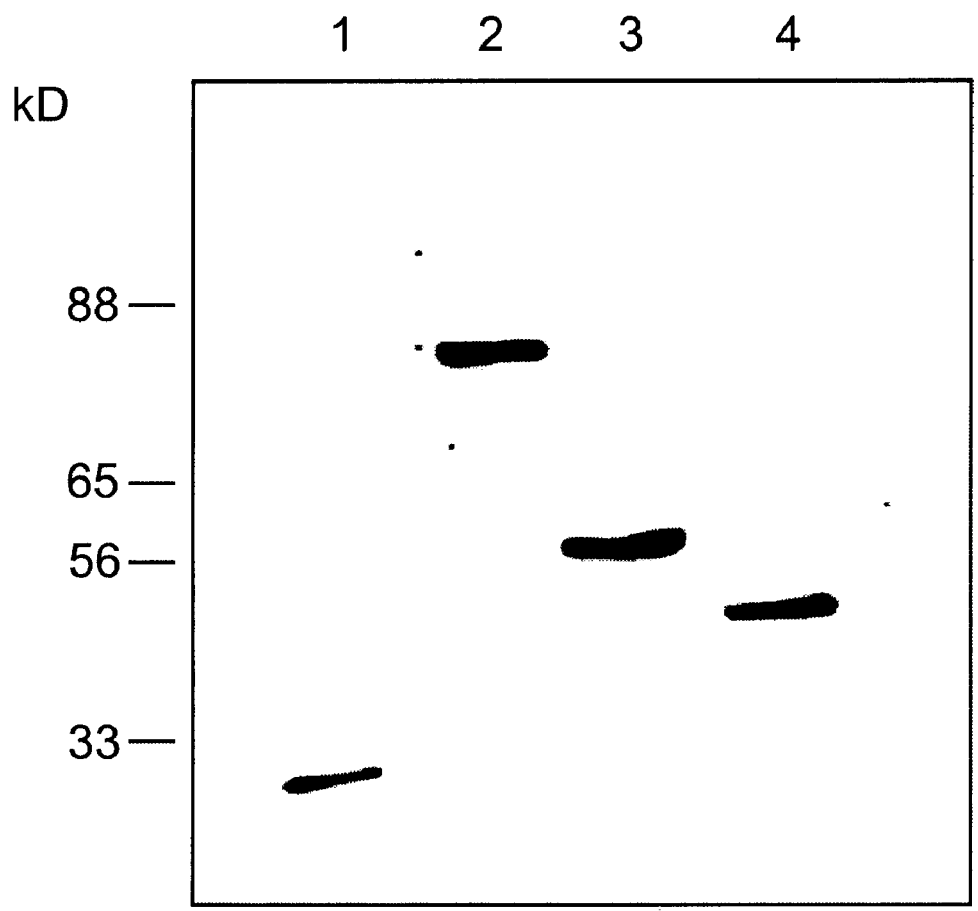

FIG. 4A is a diagrammatic depiction of the constructs used in the experiment. FIG. 4B is a depiction of expression of cytohesin-1 fusion protein in J32 cells. The cDNA segments coding for full-length cytohesin-1, SEC7- and PH domain sequences were cloned into a vaccinia virus expression vector which contained an expression cassette for intracellular Ig fusion protein expression. The constructs were recombined with wild-type vaccinia virus (WR) in CV-1 cells. Recombinant plaques were isolated and high-titer virus stock solutions were produced. $5 \times 10^6$ Jurkat J32 cells were infected therewith and incubated in RPMI medium (10% fetal bovine serum, Moore et al., *JAMA* 199: 519–24 (1967) for 4 hours. The cells were then lysed in 150 mM NaCl, 100 mM Tris Cl pH 7.5, 1% Triton-X-100, 1 mM PMSF, and the fusion proteins were bound by protein A-Sepharose® beads. Aliquots of the eluted proteins were fractionated by polyacrylamide electrophoresis and blotted onto nitrocellulose.

The fusion proteins were conjugated by incubating the filters with protein-A-peroxidase and visualized by subsequent treatment with a chemiluminescent substrate by an appropriate assay (chemiluminescence kit from Amersham: ECL-Kit, RPN-2106).

Figure 4C:
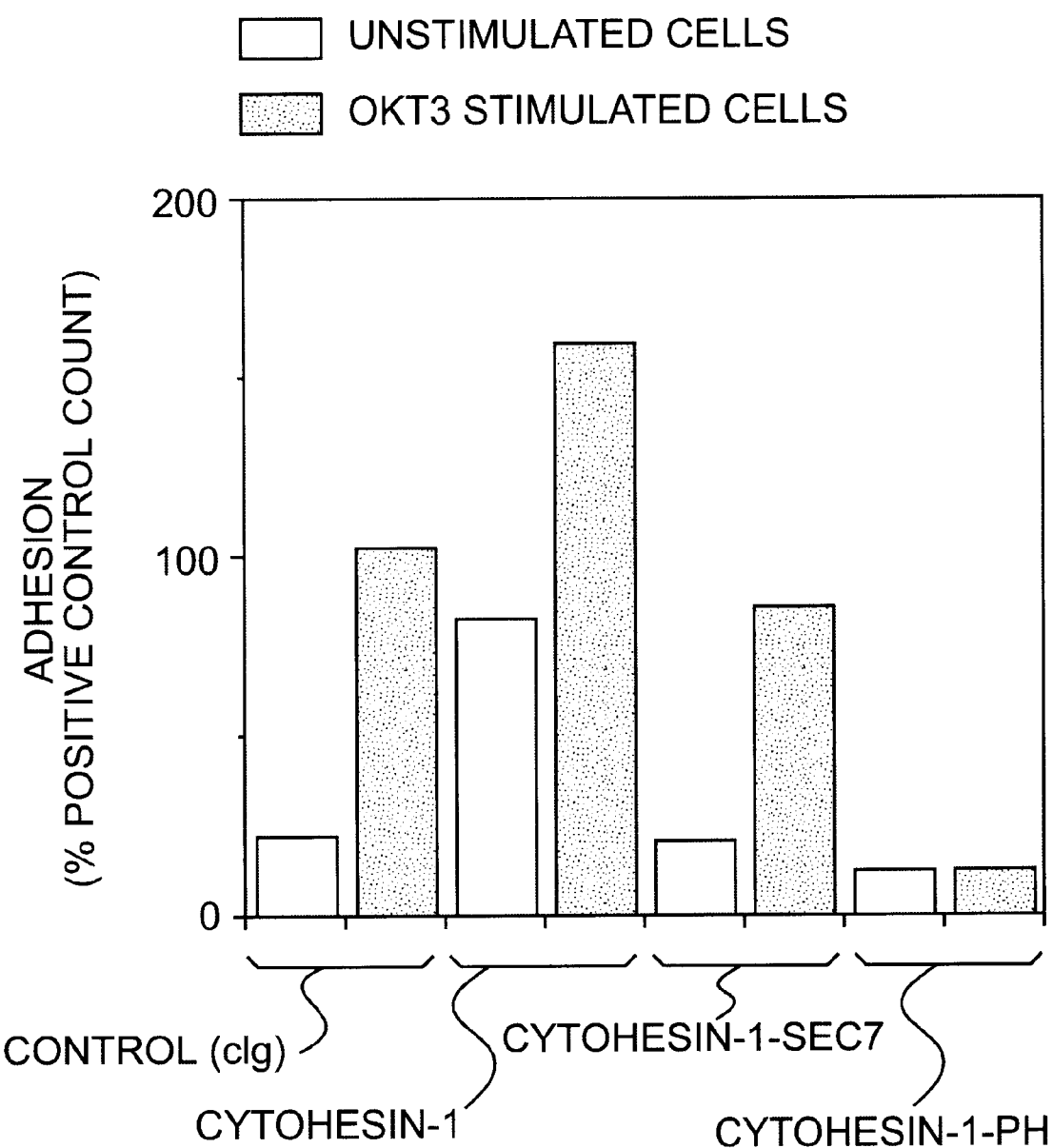

FIG. 4C depicts data from an adhesion assay. ICAM-1-Rg fusion protein was expressed in COS cells and isolated from the culture supernatant with protein A-Sepharose®, then eluted and resuspended in PBS (phosphate-buffered saline). The ICAM-1-Rg was then used to coat Falcon® 1008 plastic dishes as described by Rawlings et al., Science 261: 358–361, 1993. Jurkat 32 cells were then infected with recombinant vaccinia virus as described for FIG. 4B. Aliquots of these cells were then permeabilized using methods known to the skilled person and stained with an anti-IgG-FITC-conjugate (goat anti-human-fluorescein isothiocyanate; manufacturer: Jackson Labs; marketed by DIANOVA, Hamburg, Code: 109–095–088). Expression was observed by a cytometric flow analysis (apparatus: Coulter Epics XL); normally, more than 30% of the cells were positive. $2 \times 106$ cells were incubated in RPMI medium at 25° C. with or without addition of 3 µg/ml OKT3 antibody for 5 minutes. A comparative test with a control antibody (mIgG2b) showed no effect (data not shown). The cells treated in this way were then applied to plastic dishes coated with ICAM-1-Rg (25° C., 5 minutes), and the bound portion of the cells was determined using a microscope. The representative result of an experiment from a total of 8 independent experiments is shown.

Figure 5:
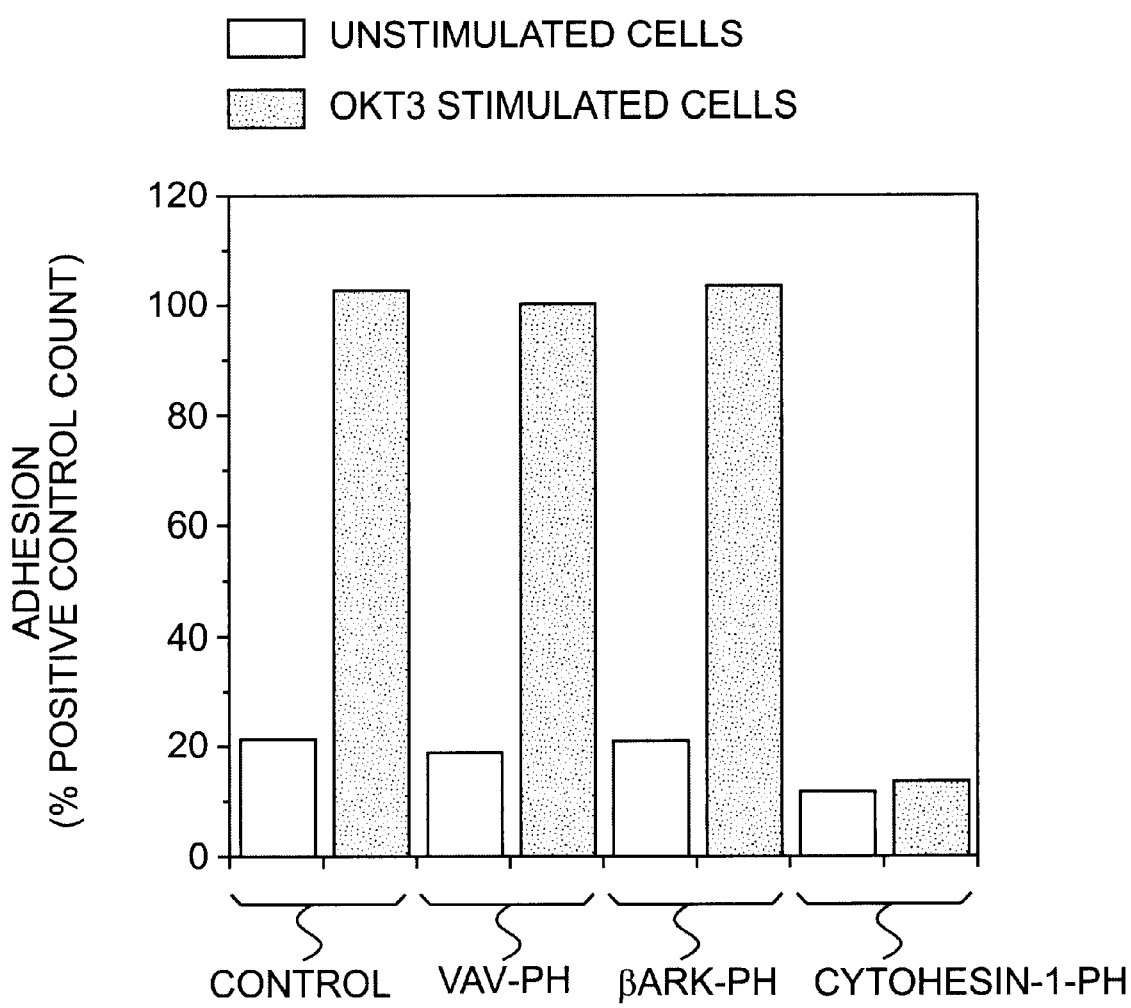
FIG. 5 depicts data from adhesion studies of the specificity of the cytohesin-1-PH domain.

In the study of FIG. 5, cDNA fragments which code for the PH domains of βark (Benovic et al., *FEBS Lett.* 283; 122-126, (1991;) Nucleotides 1763–2075) and VAV protein (Katzav et al., *EMBO J.* 8: 2283–2290 (1989); Nucleotides 1152-1484) were introduced into the vaccinia virus expression system described. The influence of the expression of the corresponding PH domains on the binding of J32 cells to ICAM-1-Rg was tested as described for the assays of FIG. 4C.

EXAMPLE 8

Preparation of the ICAM-Rg Fusion Protein

ICAM-1-Rg cDNA was expressed in cosM6 cells by DEAE-dextran transfection for 10 days (Walz et al. (1990), cosM6: subclone of cos7; origin cos7: ATCC CRL-1651; cosM6 selected for good transfectability). The supernatants were then harvested and purified using protein A-Sepharose® (Sigma). The bound protein was eluted with 4M imidazole solution and, after dialysis against PBS buffer, stored in a concentration of about 0.2 µg/ml.

Falcon® 1008 dishes were coated with a sheep anti-human antibody preparation, onto which ICAM-1-Rg was then bound in a second step (Walz, 1990). These dishes were used to determine the cytohesin function as described in EXAMPLE 7.

EXAMPLE 9

Cytohesin-PH Domain-specific Functional Inhibition of β2 Integrins

Figure 7:
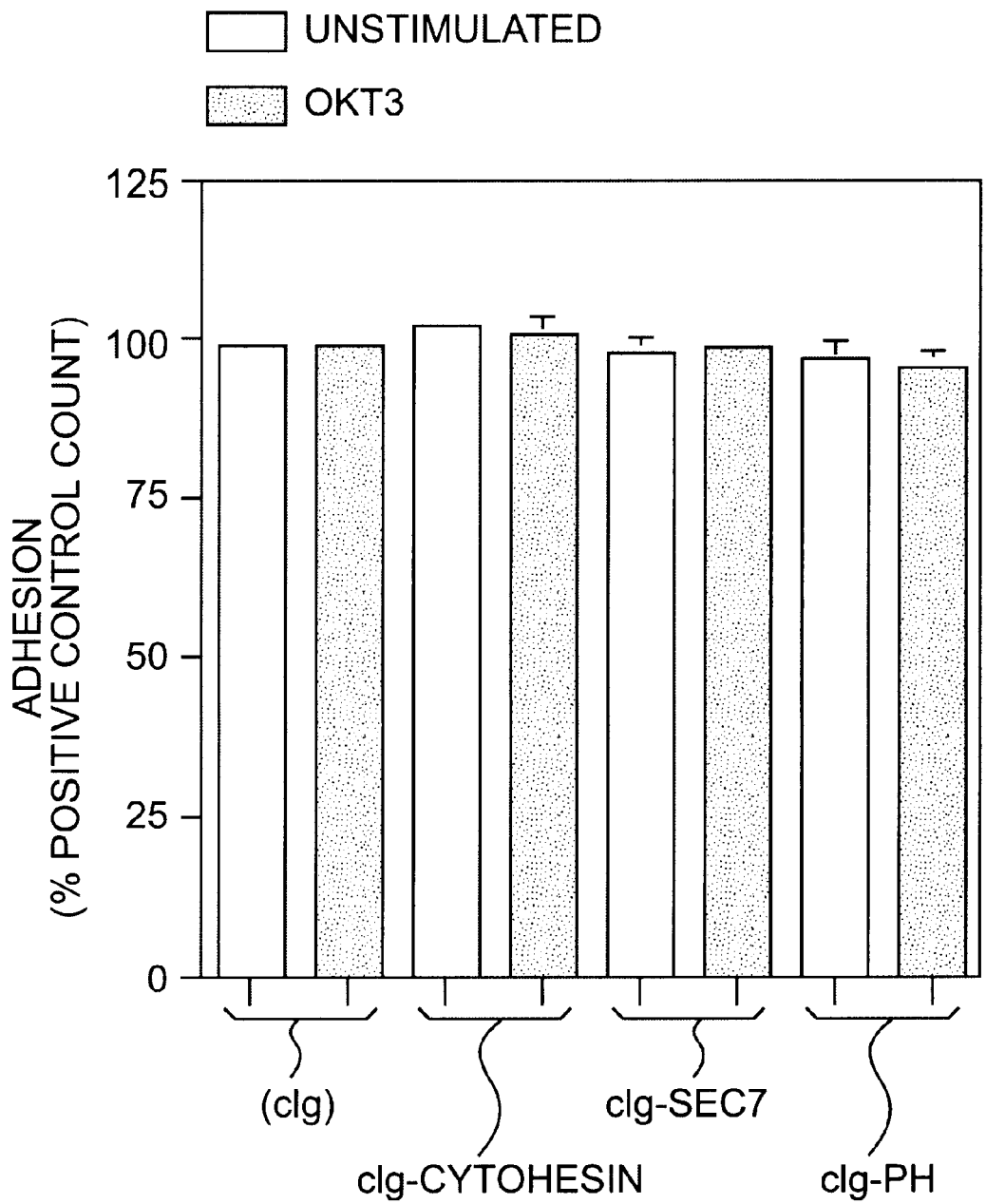
FIG. 7 depicts data from the binding of J32 cells to VCAM-1 using the constructs of EXAMPLE 6. The data show that the PH-domain does not interact with the β1-integrin. See EXAMPLE 9.

The cytohesin-PH domain specifically inhibits the function of beta-2 integrins. The binding of beta-1 integrin to its ligands VCAM-1 (Osborn et al., *Cell* 59: 1203–1211 (1989)) is unaffected by cytohesin-PH. The VCAM-1-Rg fusion protein used for the adhesion assay is constructed on the same pattern as ICAM-1-Rg. The description of the assay is identical to that in EXAMPLE 8. The cytohesin constructs are expressed as described in EXAMPLE 7. FIG. 7 shows that J32 cells bind constitutively to VCAM-1 via beta-1 integrins. Cytohesin fusion proteins of FIG. 4C show no effect on binding. Accordingly, the cytohesin-PH peptide is specific for β integrins.

It is to be understood that the description, specific examples and data, while indicating preferred embodiments, are given by way of illustration and exemplification and are not intended to limit the present invention. Various changes and modifications within the present invention will become apparent to the skilled artisan from the discussion and disclosure contained herein.

The priority application, DE 19534120.1, which was filed on Sep. 14, 1995, including its specification, claims, abstract and figures, is hereby incorporated by reference.

```

What is claimed is:

1. An isolated cytohesin-PH peptide that can inhibit the beta-2 integrins from adhering, wherein the cytohesin-PH peptide is a fragment of cytohesin-2 and comprises:

Phe Phe Asn Pro Asp Arg Glu Gly Trp Leu Leu Lys Leu Gly Gly Gly Arg Val Lys Thr Trp Lys Arg Arg Trp Phe Ile Leu Thr Asp Asn Cys Leu Tyr Tyr Phe Glu Tyr Thr Thr Asp Lys Glu Pro Arg Gly Ile Ile Pro Leu Glu Asn

Leu Ser Ile Arg Glu Val Asp Asp Pro Arg Lys Pro Asn Cys Phe Glu Leu Tyr Ile Pro Asn Asn Lys Gly Gln Leu Ile Lys Ala Cys Lys Thr Glu Ala Asp Gly Arg Val Val Glu Gly Asn His Met Val Tyr Arg Ile Ser Ala Pro Thr Gln Glu Glu Lys Asp Glu Trp Ile Lys Ser Ile Gln Ala Ala Val Ser Val Asp Pro Phe Tyr Glu Met Leu Ala Ala Arg Lys Lys Arg Ile Ser Val Lys Lys Lys Gln (positions 123–263 of SEQ ID. NO. 10).

2. An assay kit comprising a cytohesin-PH peptide that can inhibit the beta-2 integrins from adhering, wherein the cytohesin-PH peptide is a fragment of cytohesin-2 and comprises:

Phe Phe Asn Pro Asp Arg Glu Gly Trp Leu Leu Lys Ley Gly Gly Gly Arg Val Lys Thr Trp Lys Arg Arg Trp Phe Ile Leu Thr Asp Asn Cys Leu Tyr Tyr Phe Glu Tyr Thr Thr Asp Lys Glu Pro Arg Gly Ile Ile Pro Leu Glu Asn Leu Ser Ile Arg Glu Val Asp Asp Pro Arg Lys Pro Asn Cys Phe Glu Leu Tyr Ile Pro Asn Asn Lys Gly Gln Leu Ile Lys Ala Cys Lys Thr Glu Ala Asp Gly Arg Val Val Glu Gly Asn His Met Val Tyr Arg Ile Ser Ala Pro Thr Gln Gly Glu Lys Asp Gly Trp Ile Lys Ser Ile Gln Ala Ala Val Ser Val Asp Pro Phe Tyr Glu Met Leu Ala Ala Arg Lys Lys Arg Ile Ser Val Lys Lys Lys Gln (positions 123–263 of SEQ ID NO: 10).

\* \* \* \* \*

                         SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 1:

CGCGGGACGC GTGCTCTGAT CCACCTGAGC                                            30

(2) INFORMATION FOR SEQ ID NO: 2:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 2:

CGCGGGGCGG CCGCTTTAAC TCTCAGCAAA CTTGGG                                     36

(2) INFORMATION FOR SEQ ID NO: 3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 3:

CGCGGGACGC GTATGGAGGA GGACGACAGC TACGTTCCC                                  39

(2) INFORMATION FOR SEQ ID NO: 4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 4:

CGCGGGGCGG CCGCTTTAGT GTCGCTTCGT GGAGGAGACC TT                              42
```

(2) INFORMATION FOR SEQ ID NO: 5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 5:

GCGGGGACGC GTACCATGGC TAATGAAATT GAAAACCTG                39

(2) INFORMATION FOR SEQ ID NO: 6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 6:

GCGGGGGCGG CCGCTTTAGA AAGTGTGAGT GAGGTCATTC CC            42

(2) INFORMATION FOR SEQ ID NO: 7:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 7:

CGCGGGACGC GTACCATGGG TTTCAATCCA GACCGAGAAG GCTGG         45

(2) INFORMATION FOR SEQ ID NO: 8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 8:

CGCGGGGCGG CCGCTTTAGT GTCGCTTCGT GGAGGAGACC TT            42

(2) INFORMATION FOR SEQ ID NO: 9:

(i) SEQUENCE CHARACTERISTICS:
        (A) LENGTH: 263 amino acids
        (B) TYPE: amino acid
        (C) STRANDEDNESS: single
        (D) TOPOLOGY: linear (xi) SEQUENCE DESCRIPTION: SEQ ID NO: 9:

```
Phe Thr Asp Leu Asn Leu Val Gln Ala Leu Arg Gln Phe Leu Trp Ser
1               5                   10                  15

Phe Arg Leu Pro Gly Glu Ala Gln Lys Ile Asp Arg Met Met Glu Ala
            20                  25                  30

Phe Ala Gln Arg Tyr Cys Gln Cys Asn Asn Gly Val Phe Gln Ser Thr
        35                  40                  45

Asp Thr Cys Tyr Val Leu Ser Phe Ala Ile Ile Met Leu Asn Thr Ser
    50                  55                  60

Leu His Asn Pro Asn Val Lys Asp Lys Pro Thr Val Glu Arg Phe Ile
65                  70                  75                  80

Ala Met Asn Arg Gly Ile Asn Asp Gly Gly Asp Leu Pro Glu Glu Leu
```

```
                   85                  90                  95
Leu Arg Asn Leu Tyr Glu Ser Ile Lys Asn Glu Pro Phe Lys Ile Pro
                100                 105                 110

Glu Asp Asp Gly Asn Asp Leu Thr His Thr Phe Phe Asn Pro Asp Arg
                115                 120                 125

Glu Gly Trp Leu Leu Lys Leu Gly Gly Arg Val Lys Thr Trp Lys
                130                 135                 140

Arg Arg Trp Phe Ile Leu Thr Asp Asn Cys Leu Tyr Tyr Phe Glu Tyr
145                 150                 155                 160

Thr Thr Asp Lys Glu Pro Arg Gly Ile Ile Pro Leu Glu Asn Leu Ser
                165                 170                 175

Ile Arg Glu Val Glu Asp Ser Lys Lys Pro Asn Cys Phe Glu Leu Tyr
                180                 185                 190

Ile Pro Asp Asn Lys Asp Gln Val Ile Lys Ala Cys Lys Thr Glu Ala
                195                 200                 205

Asp Gly Arg Val Val Glu Gly Asn His Thr Val Tyr Arg Ile Ser Ala
                210                 215                 220

Pro Thr Pro Glu Glu Lys Glu Glu Trp Ile Lys Cys Ile Lys Ala Ala
225                 230                 235                 240

Ile Ser Arg Asp Pro Phe Tyr Glu Met Leu Ala Ala Arg Lys Lys Lys
                245                 250                 255

Val Ser Ser Thr Lys Arg His
                260

(2) INFORMATION FOR SEQ ID NO: 10:

(i) SEQUENCE CHARACTERISTICS:
        (A) LENGTH: 263 amino acids
        (B) TYPE: amino acid
        (C) STRANDEDNESS: single
        (D) TOPOLOGY: linear (xi) SEQUENCE DESCRIPTION: SEQ ID NO: 10:

Phe Thr Asp Leu Asn Leu Val Gln Ala Leu Arg Gln Phe Leu Trp Ser
1                   5                  10                  15

Phe Arg Leu Pro Gly Glu Ala Gln Lys Ile Asp Arg Met Met Glu Ala
                 20                  25                  30

Phe Ala Gln Arg Tyr Cys Leu Cys Asn Pro Gly Val Phe Gln Ser Thr
                 35                  40                  45

Asp Thr Cys Tyr Val Leu Ser Phe Ala Val Ile Met Leu Asn Thr Ser
             50                  55                  60

Leu His Asn Pro Asn Val Arg Asp Lys Pro Gly Leu Glu Arg Phe Val
65                  70                  75                  80

Ala Met Asn Arg Gly Ile Asn Glu Gly Gly Asp Leu Pro Glu Glu Leu
                 85                  90                  95

Leu Arg Asn Leu Tyr Asp Ser Ile Arg Asn Glu Pro Phe Lys Ile Pro
                100                 105                 110

Glu Asp Asp Gly Asn Asp Leu Thr His Thr Phe Phe Asn Pro Asp Arg
                115                 120                 125

Glu Gly Trp Leu Leu Lys Leu Gly Gly Arg Val Lys Thr Trp Lys
                130                 135                 140

Arg Arg Trp Phe Ile Leu Thr Asp Asn Cys Leu Tyr Tyr Phe Glu Tyr
145                 150                 155                 160

Thr Thr Asp Lys Glu Pro Arg Gly Ile Ile Pro Leu Glu Asn Leu Ser
                165                 170                 175
```

```
Ile Arg Glu Val Asp Asp Pro Arg Lys Pro Asn Cys Phe Glu Leu Tyr
            180                 185                 190

Ile Pro Asn Asn Lys Gly Gln Leu Ile Lys Ala Cys Lys Thr Glu Ala
            195                 200                 205

Asp Gly Arg Val Val Glu Gly Asn His Met Val Tyr Arg Ile Ser Ala
            210                 215                 220

Pro Thr Gln Glu Glu Lys Asp Glu Trp Ile Lys Ser Ile Gln Ala Ala
225                 230                 235                 240

Val Ser Val Asp Pro Phe Tyr Glu Met Leu Ala Ala Arg Lys Lys Arg
            245                 250                 255

Ile Ser Val Lys Lys Gln
            260

(2) INFORMATION FOR SEQ ID NO: 11:

(i) SEQUENCE CHARACTERISTICS:
        (A) LENGTH: 3311 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 70..1263

(ix) FEATURE:
        (A) NAME/KEY: mat_peptide
        (B) LOCATION: 70..1263

(xi) SEQUENCE DESCRIPTION: SEQ ID NO: 11:

GCGAGCGGGG GCGCGGGTGG CGCGGCGGGA CGCGAGCGGC GAGCCGGAGC GCGAGCCCGC          60

TCCCGCACC ATG GAG GAG GAC GAC AGC TAC GTT CCC AGT GAC CTG ACA            108
           Met Glu Glu Asp Asp Ser Tyr Val Pro Ser Asp Leu Thr
             1               5                  10

GCA GAG GAG CGT CAA GAA CTG GAG AAC ATC CGA CGG AGA AAA CAG GAG          156
Ala Glu Glu Arg Gln Glu Leu Glu Asn Ile Arg Arg Arg Lys Gln Glu
         15                  20                  25

CTG CTG GCT GAC ATT CAG AGG CTG AAG GAT GAG ATA GCA GAA GTA GCT          204
Leu Leu Ala Asp Ile Gln Arg Leu Lys Asp Glu Ile Ala Glu Val Ala
 30                  35                  40                  45

AAT GAA ATT GAA AAC CTG GGA TCC ACA GAG GAA AGG AAA AAC ATG CAG          252
Asn Glu Ile Glu Asn Leu Gly Ser Thr Glu Glu Arg Lys Asn Met Gln
             50                  55                  60

AGG AAC AAA CAG GTA GCC ATG GGC AGG AAA AAA TTT AAT ATG GAC CCT          300
Arg Asn Lys Gln Val Ala Met Gly Arg Lys Lys Phe Asn Met Asp Pro
         65                  70                  75

AAA AAG GGG ATC CAG TTC TTA ATA GAG AAC GAC CTC CTG AAG AAC ACT          348
Lys Lys Gly Ile Gln Phe Leu Ile Glu Asn Asp Leu Leu Lys Asn Thr
         80                  85                  90

TGT GAA GAC ATT GCC CAG TTC TTA TAT AAA GGC GAA GGG CTC AAC AAG          396
Cys Glu Asp Ile Ala Gln Phe Leu Tyr Lys Gly Glu Gly Leu Asn Lys
         95                  100                 105

ACA GCC ATC GGC GAC TAC CTA GGG GAG AGA GAT GAG TTT AAT ATC CAG          444
Thr Ala Ile Gly Asp Tyr Leu Gly Glu Arg Asp Glu Phe Asn Ile Gln
110                 115                 120                 125

GTT CTT CAT GCA TTT GTG GAG CTG CAT GAG TTC ACT GAT CTT AAT CTC          492
Val Leu His Ala Phe Val Glu Leu His Glu Phe Thr Asp Leu Asn Leu
             130                 135                 140

GTC CAG GCA CTA CGG CAG TTC CTG TGG AGC TTC CGG CTA CCC GGA GAG          540
Val Gln Ala Leu Arg Gln Phe Leu Trp Ser Phe Arg Leu Pro Gly Glu
         145                 150                 155
```

```
GCC CAG AAG ATC GAC CGG ATG ATG GAG GCG TTT GCC CAG CGA TAT TGT          588
Ala Gln Lys Ile Asp Arg Met Met Glu Ala Phe Ala Gln Arg Tyr Cys
        160                 165                 170

CAG TGC AAT AAT GGC GTG TTC CAG TCC ACG GAT ACT TGT TAC GTC CTC          636
Gln Cys Asn Asn Gly Val Phe Gln Ser Thr Asp Thr Cys Tyr Val Leu
175                 180                 185

TCC TTT GCC ATC ATC ATG TTG AAC ACC AGT CTG CAC AAC CCC AAT GTC          684
Ser Phe Ala Ile Ile Met Leu Asn Thr Ser Leu His Asn Pro Asn Val
190                 195                 200                 205

AAA GAT AAG CCC ACT GTG GAG AGG TTC ATT GCC ATG AAC CGA GGC ATC          732
Lys Asp Lys Pro Thr Val Glu Arg Phe Ile Ala Met Asn Arg Gly Ile
                210                 215                 220

AAT GAT GGG GGA GAC CTG CCG GAG GAG CTC CTC CGG AAT CTC TAT GAG          780
Asn Asp Gly Gly Asp Leu Pro Glu Glu Leu Leu Arg Asn Leu Tyr Glu
            225                 230                 235

AGC ATA AAA AAT GAA CCC TTT AAA ATC CCA GAA GAC GAC GGG AAT GAC          828
Ser Ile Lys Asn Glu Pro Phe Lys Ile Pro Glu Asp Asp Gly Asn Asp
        240                 245                 250

CTC ACT CAC ACT TTC TTC AAT CCA GAC CGA GAA GGC TGG CTA TTG AAA          876
Leu Thr His Thr Phe Phe Asn Pro Asp Arg Glu Gly Trp Leu Leu Lys
255                 260                 265

CTC GGA GGT GGC AGG GTA AAG ACT TGG AAG AGA CGC TGG TTC ATT CTG          924
Leu Gly Gly Gly Arg Val Lys Thr Trp Lys Arg Arg Trp Phe Ile Leu
270                 275                 280                 285

ACT GAC AAC TGC CTT TAC TAC TTT GAG TAT ACC ACG GAT AAG GAG CCC          972
Thr Asp Asn Cys Leu Tyr Tyr Phe Glu Tyr Thr Thr Asp Lys Glu Pro
                290                 295                 300

CGT GGA ATC ATC CCT TTA GAG AAT CTG AGT ATC CGG GAA GTG GAG GAC         1020
Arg Gly Ile Ile Pro Leu Glu Asn Leu Ser Ile Arg Glu Val Glu Asp
            305                 310                 315

TCC AAA AAA CCA AAC TGC TTT GAG CTT TAT ATC CCC GAC AAT AAA GAC         1068
Ser Lys Lys Pro Asn Cys Phe Glu Leu Tyr Ile Pro Asp Asn Lys Asp
        320                 325                 330

CAA GTT ATC AAG GCC TGC AAG ACC GAG GCT GAC GGG CGG GTG GTG GAG         1116
Gln Val Ile Lys Ala Cys Lys Thr Glu Ala Asp Gly Arg Val Val Glu
335                 340                 345

GGG AAC CAC ACT GTT TAC CGG ATC TCA GCT CCG ACG CCC GAG GAG AAG         1164
Gly Asn His Thr Val Tyr Arg Ile Ser Ala Pro Thr Pro Glu Glu Lys
350                 355                 360                 365

GAG GAG TGG ATT AAG TGC ATT AAA GCA GCC ATC AGC AGG GAC CCT TTC         1212
Glu Glu Trp Ile Lys Cys Ile Lys Ala Ala Ile Ser Arg Asp Pro Phe
                370                 375                 380

TAC GAA ATG CTC GCA GCA CGG AAA AAG AAG GTC TCC TCC ACG AAG CGA         1260
Tyr Glu Met Leu Ala Ala Arg Lys Lys Lys Val Ser Ser Thr Lys Arg
            385                 390                 395

CAC TGAGCGTGCA GCCAAGGGCG TTGGTCTGCG GGGGCCTTGG AGCTCCTGCT             1313
His

CTTCTCCCGC ACCTCCATGG ATGCACTGCT GCCGAGCAGA GCGTCCTCTG CCAGGCCCCG       1373

CCCTGGATTC CTAGAGACTA GCTTCAGCTT TTGCTATTTT TTTTAAGTGG GAGAAGGGTG       1433

GGCAGTTATC ACTGGGGAAG AGAGGACCGG CCACCTGTCC AGCATGGGCT CCAGAGCCTT       1493

CCTCTCTCAC AGGGCAGAGC TCTTGTCGGC AGGGCAGCCT CCTGGCCAGT TTCTCTGCTC       1553

AGTGTTCTGG TAGCAGAGCT CAGAGCCAAC TGTTTACCTC TTGGTTGTCC CCGTGAAGAA       1613

GCCTTCAAAC CCTGCACCAT AAATACATGT GTCCATATAT TATTATATGT TAAGAGAAAA       1673

AGGTGGAAAG GAAGAGAAGC CACATACTAT AAAGATCTAT TTTTTTTTTT TAAGAGAAA       1733

CGTAGGGCTG TTCAGGTGCA TTCTGCCCTG GCTGCGCTGG GGAGCTTCTC CCTGGAGAAG       1793
```

-continued

```
AGCACCTGGG GCTGCGGCCA AGGGGCATCA GCCTGGGCCC GCGGCAGGGC CTGGCCTGCC      1853

TCTCCTGTGC TGTGGGAGCT CGCTGCCTGG TGCTTGTCTT GGCGAGATGG ACAGGTGAGG      1913

TCGAGGACGC AGAGGGCAGA GGCCCAGTGG AGCCTCAGAC GGCACAGTCA GAGTCGGGGG      1973

CCTGCCTGGC CGGGGTCGCA GTCGGCAGCA GCGTGCAGTC CGGCATCTCC CGCGGATGCT      2033

TTTCCATCCC AAGTGCCTGC GGAGCCCGAG GAGAGGAGAG AGCTGACTGG ACGCTTACGT      2093

TATTTTCCTC CTTCAGAATC CAAGTTCTTG TTGGGCTTTA AAGTAGAAAG TCAGCATTTT      2153

CCTTGAGCTA AATACCTAAT AACCAAAACT GTGAGGAAGG TTATCGGGAC AGAGGTTCCG      2213

GATAACCTGT TTCATTTTGG GTTTTCTTCC TCTTCCCCAG ACTCCAGTCC TCGTTCTAGA      2273

GGAAGGAGTA GGACTTCCCC GATCCCCGTA GCTTCAGCTT TTTCTGCCTC AAAACCAGCC      2333

CTAACTGGAC TACTCTGGAT GCATTTTGTG GTGGGCCCCC TAGAGGGAAG ATGGGCCTTT      2393

ATCTGCTCCG TGGGGTGCAC TGGAGTGAGG GGGGTGGCCG GGCTGCCTCT CGCATCTCTG      2453

TCTTCCCCTG CAGGCGCTGT GTGAGCTGGC CCTGCCCCTC CTCATTACAG TATGAAGGGA      2513

GCCGTGACAC GCAGCATTTT CCTGCCGTTC TCTCAGGGAC TCTCAGGGCA GCTCCTGCCA      2573

CTCCGCCAGG GCCAGCATGC CAGTCCAGGC AGAGCAGGTG GCTGGCTGTC TGGCCGTCTC      2633

GCCCCGCCCC TCCACAGGAC CCTGGACCAG GGCGGTGCAG GGCGCAGCCC CGAGGAGGCA      2693

GGTGGAGGAG CTGCGGGTTT TCACAGGGCC GCGTCGCCAC GGCTCCTCTG ATCCTTTAGG      2753

GTTGGCGAGC ATCTCTGGAA ATAGCTTTTG CAGAGGAGTG GTGGGAGGAA TAGAGGGGGA      2813

CAGTCTGTCA CCTCCCTCCC CGCCACTTTG TGTAGATCCT ACCTGGAGGG AATGGCTTTA      2873

GGCACTTTTG TGCCAGAGCT TGTGAGGGTG ACAGAAGAGG GTCCAGGCTG GAAACCTGAA      2933

CTTTCTGGGT GGGAGAACCA GGTGGTGCCT GCCGAGGTCT GGGCGTGTTT GGGCCGGTGC      2993

TGGAGCCTGT CCAGCTGGCC CGGGCCCTGG CCTGGTTCTC AAGTGTTTCC TAGACAGAGA      3053

GGCACCTGGG TCAGTATTAG TCTATTTATC AGAGGTGTAA ATAATCTATG TATAGTTTTT      3113

CTCCTTTTAG ATTATTTTGT ATTTGTTTAA AAGAAGTTTT GTCAAAATAC AAAAATATAA      3173

AGAAATGACT GAAAGTTGTT GACAGGGTTT TTAAGAAATA ATTATTCTAA TTGTTTTTGT      3233

TTGTTTGTTT TTGCCTTGTA AACTAGCGCC AAGGAACTGC AGCAAATAAA CTCCAACTCT      3293

GCCCAAGCAA AAAAAAA                                                     3311
```

(2) INFORMATION FOR SEQ ID NO: 12:

(i) SEQUENCE CHARACTERISTICS:
        (A) LENGTH: 398 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Glu Glu Asp Asp Ser Tyr Val Pro Ser Asp Leu Thr Ala Glu Glu
 1               5                  10                  15

Arg Gln Glu Leu Glu Asn Ile Arg Arg Arg Lys Gln Glu Leu Leu Ala
                20                  25                  30

Asp Ile Gln Arg Leu Lys Asp Glu Ile Ala Glu Val Ala Asn Glu Ile
            35                  40                  45

Glu Asn Leu Gly Ser Thr Glu Glu Arg Lys Asn Met Gln Arg Asn Lys
        50                  55                  60

Gln Val Ala Met Gly Arg Lys Lys Phe Asn Met Asp Pro Lys Lys Gly
 65                  70                  75                  80
```

```
Ile Gln Phe Leu Ile Glu Asn Asp Leu Leu Lys Asn Thr Cys Glu Asp
                85                  90                  95

Ile Ala Gln Phe Leu Tyr Lys Gly Glu Gly Leu Asn Lys Thr Ala Ile
               100                 105                 110

Gly Asp Tyr Leu Gly Glu Arg Asp Glu Phe Asn Ile Gln Val Leu His
               115                 120                 125

Ala Phe Val Glu Leu His Glu Phe Thr Asp Leu Asn Leu Val Gln Ala
       130                 135                 140

Leu Arg Gln Phe Leu Trp Ser Phe Arg Leu Pro Gly Glu Ala Gln Lys
145                 150                 155                 160

Ile Asp Arg Met Met Glu Ala Phe Ala Gln Arg Tyr Cys Gln Cys Asn
               165                 170                 175

Asn Gly Val Phe Gln Ser Thr Asp Thr Cys Tyr Val Leu Ser Phe Ala
       180                 185                 190

Ile Ile Met Leu Asn Thr Ser Leu His Asn Pro Asn Val Lys Asp Lys
       195                 200                 205

Pro Thr Val Glu Arg Phe Ile Ala Met Asn Arg Gly Ile Asn Asp Gly
   210                 215                 220

Gly Asp Leu Pro Glu Glu Leu Leu Arg Asn Leu Tyr Glu Ser Ile Lys
225                 230                 235                 240

Asn Glu Pro Phe Lys Ile Pro Glu Asp Asp Gly Asn Asp Leu Thr His
               245                 250                 255

Thr Phe Phe Asn Pro Asp Arg Glu Gly Trp Leu Leu Lys Leu Gly Gly
               260                 265                 270

Gly Arg Val Lys Thr Trp Lys Arg Arg Trp Phe Ile Leu Thr Asp Asn
       275                 280                 285

Cys Leu Tyr Tyr Phe Glu Tyr Thr Thr Asp Lys Glu Pro Arg Gly Ile
       290                 295                 300

Ile Pro Leu Glu Asn Leu Ser Ile Arg Glu Val Glu Asp Ser Lys Lys
305                 310                 315                 320

Pro Asn Cys Phe Glu Leu Tyr Ile Pro Asp Asn Lys Asp Gln Val Ile
               325                 330                 335

Lys Ala Cys Lys Thr Glu Ala Asp Gly Arg Val Val Glu Gly Asn His
               340                 345                 350

Thr Val Tyr Arg Ile Ser Ala Pro Thr Pro Glu Glu Lys Glu Glu Trp
       355                 360                 365

Ile Lys Cys Ile Lys Ala Ala Ile Ser Arg Asp Pro Phe Tyr Glu Met
       370                 375                 380

Leu Ala Ala Arg Lys Lys Lys Val Ser Ser Thr Lys Arg His
385                 390                 395
```

(2) INFORMATION FOR SEQ ID NO: 13:

(i) SEQUENCE CHARACTERISTICS:
        (A) LENGTH: 1009 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: (1..804)

(ix) FEATURE:
        (A) NAME/KEY: mat_peptide
        (B) LOCATION: (1..804)

(xi) SEQUENCE DESCRIPTION: SEQ ID NO: 13:

```
CAT GAG TTC ACC GAC CTC AAT CTG GTG CAG TCC CTC AGG CAG TTT CTA         48
His Glu Phe Thr Asp Leu Asn Leu Val Gln Ser Leu Arg Gln Phe Leu
 1               5                  10                  15

TGG AGC TTT CGC CTA CCC GGA GAG GCC CAG AAA ATT GAC CGG ATG ATG         96
Trp Ser Phe Arg Leu Pro Gly Glu Ala Gln Lys Ile Asp Arg Met Met
             20                  25                  30

GAG GCC TTC GCC CAG CGA TAC TGC CTG TGC AAC CCT GGG GTT TTC CAG        144
Glu Ala Phe Ala Gln Arg Tyr Cys Leu Cys Asn Pro Gly Val Phe Gln
         35                  40                  45

TCC ACA GAC ACG TGC TAT GTG CTG TCC TTC GCC GTC ATC ATG CTC AAC        192
Ser Thr Asp Thr Cys Tyr Val Leu Ser Phe Ala Val Ile Met Leu Asn
     50                  55                  60

ACC AGT CTC CAC AAT CCC AAT GTC CGG GAC AAG CCG GGC CTG GAG CGC        240
Thr Ser Leu His Asn Pro Asn Val Arg Asp Lys Pro Gly Leu Glu Arg
 65                  70                  75                  80

TTT GTG GCC ATG AAC CGG GGC ATC AAC GAG GGC GGG GAC CTG CCT GAG        288
Phe Val Ala Met Asn Arg Gly Ile Asn Glu Gly Gly Asp Leu Pro Glu
             85                  90                  95

GAG CTG CTC AGG AAC CTG TAC GAC AGC ATC CGA AAT GAG CCC TTC AAG        336
Glu Leu Leu Arg Asn Leu Tyr Asp Ser Ile Arg Asn Glu Pro Phe Lys
        100                 105                 110

ATT CCT GAG GAT GAC GGG AAT GAC CTG ACC CAC ACC TTC TTC AAC CCG        384
Ile Pro Glu Asp Asp Gly Asn Asp Leu Thr His Thr Phe Phe Asn Pro
    115                 120                 125

GAC CGG GAG GGC TGG CTC CTG AAG CTG GGA GGG GGC CGG GTG AAG ACG        432
Asp Arg Glu Gly Trp Leu Leu Lys Leu Gly Gly Gly Arg Val Lys Thr
130                 135                 140

TGG AAG CGG CGC TGG TTT ATC CTC ACA GAC AAC TGC CTC TAC TAC TTT        480
Trp Lys Arg Arg Trp Phe Ile Leu Thr Asp Asn Cys Leu Tyr Tyr Phe
145                 150                 155                 160

GAG TAC ACC ACG GAC AAG GAG CCC CGA GGA ATC ATC CCC CTG GAG AAT        528
Glu Tyr Thr Thr Asp Lys Glu Pro Arg Gly Ile Ile Pro Leu Glu Asn
                165                 170                 175

CTG AGC ATC CGA GAG GTG GAC GAC CCC CGG AAA CCG AAC TGC TTT GAA        576
Leu Ser Ile Arg Glu Val Asp Asp Pro Arg Lys Pro Asn Cys Phe Glu
            180                 185                 190

CTT TAC ATC CCC AAC AAC AAG GGG CAG CTC ATC AAA GCC TGC AAA ACT        624
Leu Tyr Ile Pro Asn Asn Lys Gly Gln Leu Ile Lys Ala Cys Lys Thr
        195                 200                 205

GAG GCG GAC GGC CGA GTG GTG GAG GGA AAC CAC ATG GTG TAC CGG ATC        672
Glu Ala Asp Gly Arg Val Val Glu Gly Asn His Met Val Tyr Arg Ile
    210                 215                 220

TCG GCC CCC ACA CAG GAG GAG AAG GAC GAG TGG ATC AAG TCC ATC CAG        720
Ser Ala Pro Thr Gln Glu Glu Lys Asp Glu Trp Ile Lys Ser Ile Gln
225                 230                 235                 240

GCG GCT GTG AGT GTG GAC CCC TTC TAT GAG ATG CTG GCA GCG AGA AAG        768
Ala Ala Val Ser Val Asp Pro Phe Tyr Glu Met Leu Ala Ala Arg Lys
                245                 250                 255

AAG CGG ATT TCA GTC AAG AAG AAG CAG GAG CAG CCC TGACCCCCTG             814
Lys Arg Ile Ser Val Lys Lys Lys Gln Glu Gln Pro
```

-continued

```
              260         265
CCCCCAACTC CATTATTTAT TACGGAGCTG CCCCGCCTGG GTGGCCGGAC         864

CCCTGGGCCT TGGGGCTGTG GATCCTGGTT CCCTGTTTGG AAAATTCACC         914

ACCTCTAGCT CCTCACTGTT CTTTGTAATT AACACGCTGT TGGTAATCTT         964

ATTAATTATT TAAAAAAAAA AAAAAAAAAA AAAAAAAAAC TCGAG             1009
```

(2) INFORMATION FOR SEQ ID NO: 14:

(i) SEQUENCE CHARACTERISTICS:
        (A) LENGTH: 268 amino acids
        (B) TYPE: amino acid
        (D) TOPOLOGY: linear (ii) MOLECULE TYPE: protein (xi) SEQUENCE DESCRIPTION: SEQ ID NO: 14:

```
His Glu Phe Thr Asp Leu Asn Leu Val Gln Ser Leu Arg Gln Phe Leu
 1               5                  10                  15

Trp Ser Phe Arg Leu Pro Gly Glu Ala Gln Lys Ile Asp Arg Met Met
            20                  25                  30

Glu Ala Phe Ala Gln Arg Tyr Cys Leu Cys Asn Pro Gly Val Phe Gln
        35                  40                  45

Ser Thr Asp Thr Cys Tyr Val Leu Ser Phe Ala Val Ile Met Leu Asn
    50                  55                  60

Thr Ser Leu His Asn Pro Asn Val Arg Asp Lys Pro Gly Leu Glu Arg
65                  70                  75                  80

Phe Val Ala Met Asn Arg Gly Ile Asn Glu Gly Gly Asp Leu Pro Glu
                85                  90                  95

Glu Leu Leu Arg Asn Leu Tyr Asp Ser Ile Arg Asn Glu Pro Phe Lys
            100                 105                 110

Ile Pro Glu Asp Asp Gly Asn Asp Leu Thr His Thr Phe Phe Asn Pro
        115                 120                 125

Asp Arg Glu Gly Trp Leu Leu Lys Leu Gly Gly Arg Val Lys Thr
    130                 135                 140

Trp Lys Arg Arg Trp Phe Ile Leu Thr Asp Asn Cys Leu Tyr Tyr Phe
145                 150                 155                 160

Glu Tyr Thr Thr Asp Lys Glu Pro Arg Gly Ile Ile Pro Leu Glu Asn
                165                 170                 175

Leu Ser Ile Arg Glu Val Asp Asp Pro Arg Lys Pro Asn Cys Phe Glu
            180                 185                 190

Leu Tyr Ile Pro Asn Asn Lys Gly Gln Leu Ile Lys Ala Cys Lys Thr
        195                 200                 205

Glu Ala Asp Gly Arg Val Val Glu Gly Asn His Met Val Tyr Arg Ile
    210                 215                 220

Ser Ala Pro Thr Gln Glu Glu Lys Asp Glu Trp Ile Lys Ser Ile Gln
225                 230                 235                 240

Ala Ala Val Ser Val Asp Pro Phe Tyr Glu Met Leu Ala Ala Arg Lys
                245                 250                 255

Lys Arg Ile Ser Val Lys Lys Gln Glu Gln Pro
            260                 265
```